(12) United States Patent
Ryan et al.

(10) Patent No.: US 9,021,894 B2
(45) Date of Patent: *May 5, 2015

(54) DETECTING ANOMALOUS WEAK BEOL SITES IN A METALLIZATION SYSTEM

(75) Inventors: Vivian W. Ryan, Berne, NY (US); Holm Geisler, Dresden (DE); Dirk Breuer, Dresden (DE)

(73) Assignee: GLOBALFOUNDRIES Inc., Grand Cayman (KY)

( * ) Notice: Subject to any disclaimer, the term of this patent is extended or adjusted under 35 U.S.C. 154(b) by 266 days.

This patent is subject to a terminal disclaimer.

(21) Appl. No.: 13/560,337

(22) Filed: Jul. 27, 2012

(65) Prior Publication Data

US 2014/0026676 A1      Jan. 30, 2014

(51) Int. Cl.
*G01L 1/22* (2006.01)
*G01N 3/00* (2006.01)
*H01L 21/66* (2006.01)
*H01L 23/00* (2006.01)

(52) U.S. Cl.
CPC *G01N 3/00* (2013.01); *H01L 22/12* (2013.01); *H01L 24/14* (2013.01); *H01L 2924/3511* (2013.01); *G01N 2203/0286* (2013.01); *H01L 23/562* (2013.01); *H01L 24/11* (2013.01); *H01L 24/13* (2013.01); *H01L 2224/13018* (2013.01); *H01L 2224/13147* (2013.01); *H01L 2224/14517* (2013.01); *H01L 2224/16227* (2013.01); *H01L 2224/1184* (2013.01)

(58) Field of Classification Search
USPC .......................................................... 73/862
See application file for complete search history.

(56) References Cited

U.S. PATENT DOCUMENTS

| 5,929,521 | A | 7/1999 | Wark et al. |
| 6,774,651 | B1 | 8/2004 | Hembree |
| 8,198,131 | B2 | 6/2012 | Weng et al. |
| 8,479,578 | B2 * | 7/2013 | Geisler et al. ................... 73/627 |
| 8,623,754 | B1 | 1/2014 | Ryan et al. |
| 2003/0141889 | A1 | 7/2003 | Chen et al. |
| 2004/0088855 | A1 | 5/2004 | Akram |
| 2010/0052174 | A1 | 3/2010 | Bachman et al. |
| 2014/0026676 | A1 | 1/2014 | Ryan et al. |

OTHER PUBLICATIONS

Office Action from related U.S. Appl. No. 14/083,962 dated Feb. 14, 2014.
Office Action from related U.S. Appl. No. 13/560,120 dated Apr. 18, 2014.

* cited by examiner

*Primary Examiner* — Lisa Caputo
*Assistant Examiner* — Octavia D. Hollington
(74) *Attorney, Agent, or Firm* — Amerson Law Firm, PLLC

(57) ABSTRACT

Generally, the subject matter herein relates to detecting the presence of weak BEOL sites in a metallization system. One disclosed method includes performing a lateral force test on a pillar bump formed above a metallization system of a semiconductor chip, which includes contacting the pillar bump with a test probe while moving the test probe at a substantially constant speed that is less than approximately 1 μm/sec along a path that is oriented at a substantially non-zero angle relative to a plane of the metallization system. Furthermore, the test probe is moving substantially away from the metallization system so that a force imposed on the pillar bump by the test probe has an upward component that induces a tensile load on the metallization system. The disclosed method also includes determining a behavioral interaction between the pillar bump and the metallization system during the lateral force test.

20 Claims, 15 Drawing Sheets

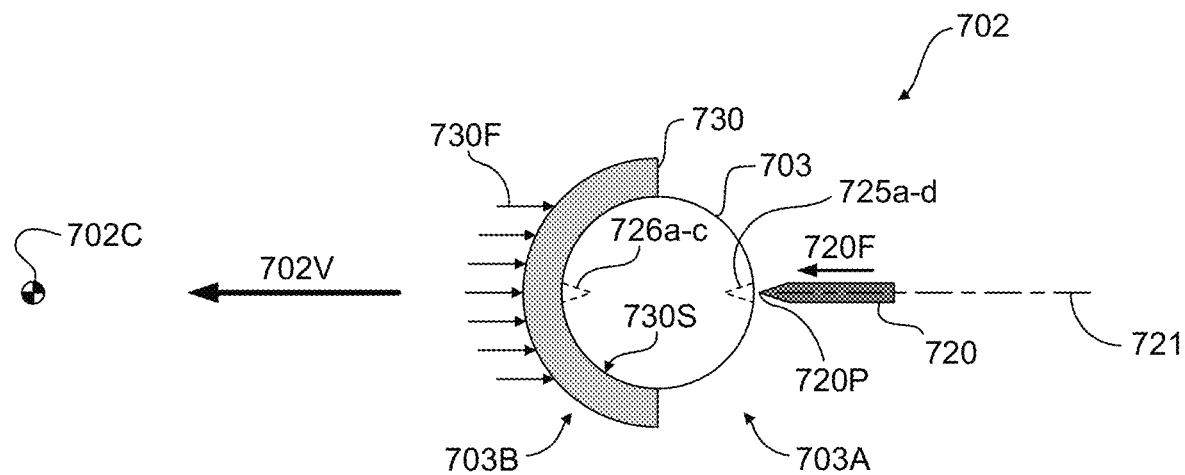
Fig. 7c
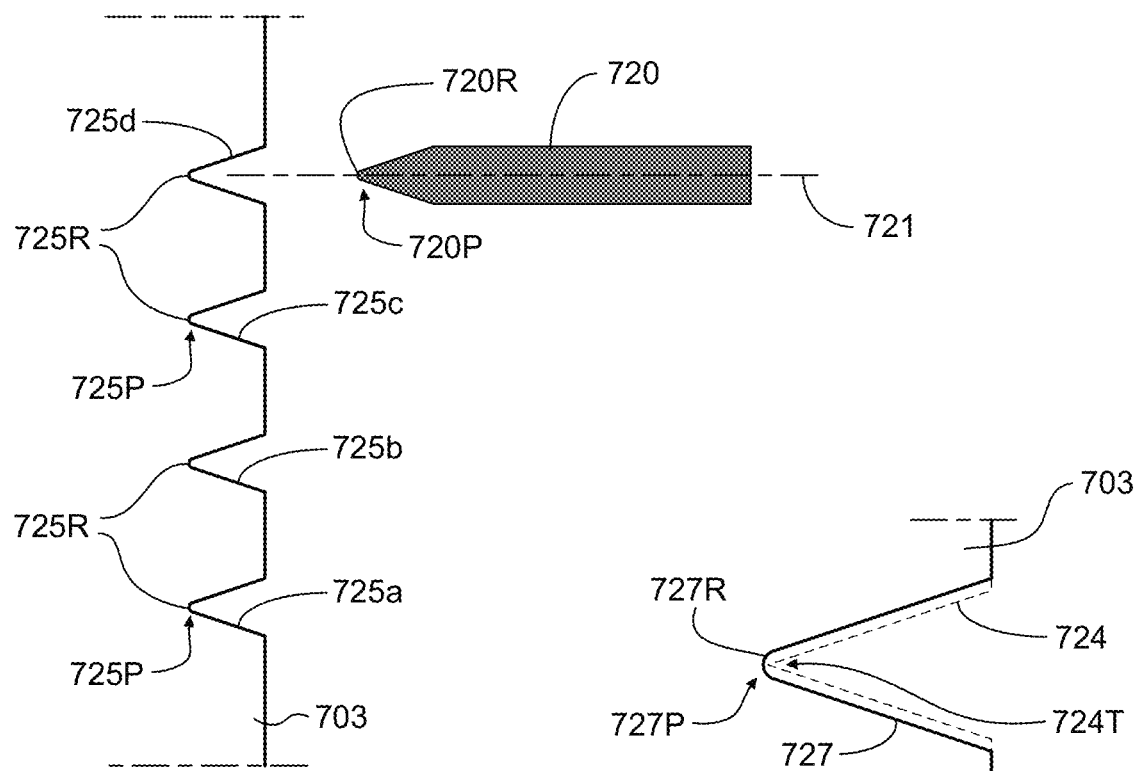
Fig. 7d
Fig. 7e

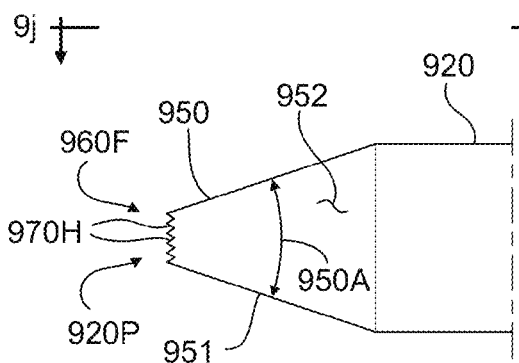
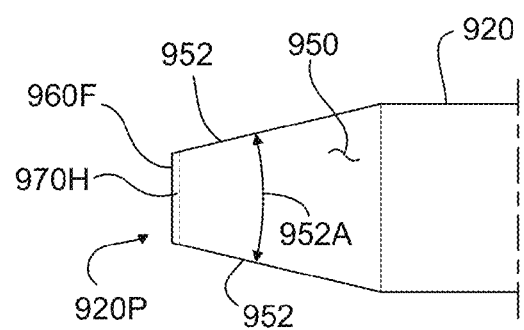
Fig. 9i
Fig. 9j
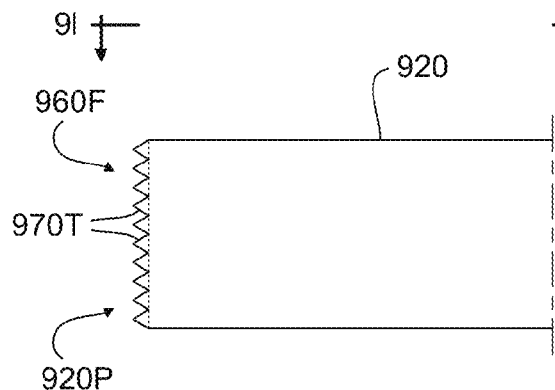
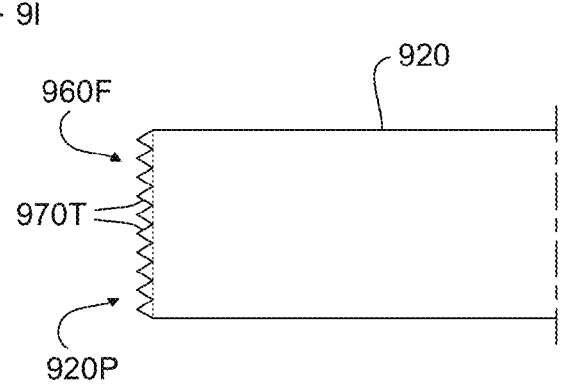
Fig. 9k
Fig. 9l

DETECTING ANOMALOUS WEAK BEOL SITES IN A METALLIZATION SYSTEM

BACKGROUND

1. Field of the Disclosure

Generally, the present disclosure relates to sophisticated semiconductor devices, and, more particularly, to methods and systems for testing and evaluating the metallization layers of a back-end-of-line (BEOL) metallization system and the pillar bumps that may be formed thereabove.

2. Description of the Related Art

In modern ultra-high density integrated circuits, device features have been steadily decreasing in size to enhance the performance of the semiconductor device and the overall functionality of the circuit. In addition to an increase in the speed of operation due to reduced signal propagation times, reduced feature sizes allow an increase in the number of functional elements in the circuit in order to extend its functionality. Moreover, even as overall device sizes have dramatically decreased, the manufacturers of advanced semiconductor devices remain under constant pressure to reduce both costs and manufacturing times so as to remain economically competitive.

In the manufacture of many sophisticated integrated circuits, it is usually necessary to provide electrical connections between the various semiconductor chips making up a microelectronic device. Depending on the type of chip and the overall device design requirements, these electrical connections may be accomplished in a variety of ways, such as, for example, by wirebonding, tape automated bonding (TAB), flip-chip bonding, and the like. In recent years, the use of flip-chip technology, wherein semiconductor chips are attached to carrier substrates, or to other chips, by means of solder balls formed from so-called solder bumps, has become an important aspect of the semiconductor processing industry.

In flip-chip technology, solder balls are formed on a contact layer of at least one of the chips that is to be connected, such as, for example, on a dielectric passivation layer formed above the last metallization layer of a semiconductor chip that includes a plurality of integrated circuits. Similarly, adequately sized and appropriately located bond pads are formed on another chip, such as, for example, a carrier package substrate, such that each bond pad corresponds to a respective solder ball formed on the semiconductor chip. The two units, i.e., the semiconductor chip and carrier substrate, are then electrically connected by "flipping" the semiconductor chip, bringing the solder balls into physical contact with the bond pads, and performing a so-called Controlled Collapse Chip Connection (C4) solder bump "reflow" process at high-temperature, so that each solder ball on the semiconductor chip melts and bonds to a corresponding bond pad on the carrier substrate. Typically, hundreds of solder bumps may be distributed over the entire chip area, thereby providing, for example, the I/O capability required for modern semiconductor chips that usually include complex circuitry, such as microprocessors, storage circuits, three-dimensional (3D) chips, and the like, and/or a plurality of integrated circuits forming a complete complex circuit system.

As semiconductor devices have gradually been reduced in size over successive design technology node generations, pillar bumps made up of more highly conductive materials, such as copper, gold, silver and/or alloys thereof, have replaced solder bumps in at least some flip-chip and 3D chip applications. Pillar bumps offer several advantages over more traditional solder bump connections, including higher interconnect densities, improved electrical and thermal performance, a greater standoff between the chip and the substrate, easier underfilling after the bonding operation, greater device reliability, and the like. During a typical high temperature C4 solder bump reflow process, solder bumps will generally collapse and spread out to some degree, thereby changing shape and size during the bonding process. Pillar bumps, on the other hand, which may only have relatively small solder caps for bonding to the corresponding bonding pads, substantially retain their shape and dimensional stability during the reflow process, due in most part to the higher melting temperatures of a typical pillar bump material, such as copper and the like, as compared to that of a typical solder material. This improvement in dimensional stability in turn permits the fabrication of pillar bumps based on much tighter bump pitches than would commonly be used for solder bumps, and an some cases much finer redistribution wiring patterns, thus leading to higher interconnect densities.

As noted above, pillar bumps sometimes have a small solder cap, which may be used to bond the pillar bumps to respective bond pads on a corresponding carrier substrate during a high temperature reflow process. Typically, the carrier substrate material is an organic laminate, which has a coefficient of thermal expansion (CTE) that may be on the order of anywhere from 4-8 times greater than that of the semiconductor chip, which, in many cases, is made up primarily of silicon and silicon-based materials. Accordingly, due to the CTE mismatch between the semiconductor chip and the carrier substrate (i.e., silicon vs. organic laminate), the carrier substrate will grow more than the semiconductor chip when exposed to the reflow temperature, and as a consequence, thermal interaction stresses will be imposed on the chip/substrate package as the package cools and the solder caps solidify. FIGS. 1a-1d, which schematically illustrate at least some of the possible chip packaging thermal interaction effects that may occur during this process, will now be described.

FIG. 1a schematically illustrates a chip package 100, which includes a carrier substrate 101 and a semiconductor chip 102. The semiconductor chip 102 typically includes a plurality of pillar bumps 103, which are formed above a metallization system 104 (see FIG. 1d) of the chip 102. In at least some cases, the pillar bumps 103 include solder caps 103C, which generally facilitate the bonding operation between the pillar bumps 103 and corresponding bond pads (not shown) on the carrier substrate 101. During the chip packaging assembly process, the semiconductor chip 102 is inverted, or "flipped," and brought into contact the carrier substrate 101, after which the chip package 100 of FIG. 1a is exposed to a reflow process 120 at a reflow temperature that exceeds the melting temperature of the material making up the solder caps 103C. Depending on the specific solder alloy used to form the solder caps 103C, the reflow temperature may be upwards of 200°-265° C. During the reflow process 120, when the material of the solder caps 103C is in a liquid phase, both the carrier substrate 101 and the semiconductor chip 102 are able to thermally "grow" in a substantially unrestrained manner, based on the coefficient of thermal expansion of each respective component. As such, both the carrier substrate 101 and the semiconductor chip 102 remain in an essentially flat, non-deformed condition, although each will grow by a different amount due to their different CTE's.

FIG. 1b, on the other hand, schematically illustrates the chip package 100 during a cool-down phase, when a thermal interaction begins to take place between the carrier substrate 101 and the semiconductor chip 102. As the chip package 100 cools, the solder caps 103C solidify and mechanically join the pillar bumps 103 on the semiconductor chip 102 to the bond pads on the carrier package substrate 101. As the chip package 100 continues to cool after solder cap 103C solidification, the CTE mismatch between the materials of the carrier substrate 101 and the semiconductor chip 102 cause the substrate 101 to shrink at a greater rate than the chip 102. Typically, this difference in thermal expansion/contraction is accommodated by a combination of out-of-plane deformation of both the carrier substrate 101 and the semiconductor chip 102, and some amount of shear deformation of the pillar bumps 103. This out-of-plane deformation induces shear and bending forces 101F, 101M in the carrier substrate 101, as well as shear and bending forces 102F, 102M in the semiconductor chip 102. Other localized effects may occur in the semiconductor chip 102 in areas immediately surrounding the pillar bumps 103, as illustrated in FIG. 1d and described below.

FIG. 1c schematically illustrates a plan view of the semiconductor chip 102 of FIGS. 1a-1b. As shown in FIG. 1c, the semiconductor chip 102 has a center 102C located at the intersection of an first chip centerline 102X and a second chip centerline 102Y of the chip 102. Additionally, a plurality of pillar bumps 103 may be distributed over the surface of the semiconductor chip 102. It should be noted, however, that while the pillar bumps 103 shown in FIG. 1c are depicted as being randomly positioned, it should be appreciated that the relative positions of the pillar bumps 103 are illustrative only, as the bumps 103 may generally be distributed in a substantially uniform or homogeneous fashion, at least locally, over the surface of the semiconductor chip 102. Furthermore, the schematically depicted shear force 102F that may be induced in semiconductor chip 102 as a result of the thermal interaction between the chip 102 and the carrier substrate 101 (see, FIG. 1b) will generally be oriented from the periphery 102P of the semiconductor chip 102 toward, or in the general direction of, the center 102C, as indicated by the arrows shown in FIG. 1c.

FIG. 1d schematically illustrates an area of the semiconductor chip 102 surrounding an individual pillar bump 103A after cool-down of the chip package 100. For simplicity, the semiconductor chip 102 has been inverted relative to the chip packaging configurations illustrated in FIGS. 1a-1b, and the carrier substrate 101 is not shown. Furthermore, only the uppermost metallization layers 104A, 104B and 104C of a metallization system 104 of the semiconductor chip 102 are shown in FIG. 1d, and any metallization layers below layer 104C, device layers, or substrate layers of the chip 102 have not been depicted. The semiconductor chip 102 may include a passivation layer 106 formed above the last metallization layer 104A, an underbump metallization (UBM) layer 105U formed in and above an opening in the passivation layer 106, and a pillar bump 103A formed above the UBM layer 105U. In some cases, the pillar bump 103A may facilitate the creation of an electrical connection between the carrier substrate 101 (not shown in FIG. 1d) and one or more semiconductor devices (not shown) formed in the device level (not shown) of the semiconductor chip 102. However, in other cases, the pillar bump 103A may be a "dummy bump" that does not provide an electrical connection to chip circuitry (not shown), but wherein the "dummy bump" is included so as to provide the substantially uniform or homogeneous bump distribution previously noted.

When the pillar bump 103A is intended to provide an electrical connection to chip circuitry (not shown in FIG. 1d), the UBM layer 105U and the pillar bump 103A may be formed above a bond pad 105, which may be used to facilitate an electrical connection to an underlying contact structure 107. Both the bond pad 105 and the contact structure 107 shown in FIG. 1d are outlined with dotted lines, indicating that these elements may or may not be present below the pillar bump 103A. As noted previously, the bond pad 105 (when present) may be in contact with the contact structure 107 so as to facilitate the electrical connection of the pillar bump 103A to an integrated circuit (not shown) formed in the device level (not shown) below the metallization system 104. For illustrative purposes only, the contact structure 107 (when present) may include, for example, a contact via 107B formed in the metallization layer 104B, a conductive line 107C and a contact via 107D in the metallization layer 104C, and the like, whereas other configurations may also be used.

As noted above, during the cool-down phase, the out-of-plane deformation of the chip package 100 that is caused by the thermal interaction of the semiconductor chip 102 and the carrier substrate 101 will typically induce shear and bending forces 102F, 102M in the chip 102. These shear and bending forces 102F, 102M will result in localized loads acting on each pillar bump 103, such as a shear load 103S, a tensile or uplift load 103T and bending moment 103M across the pillar bump 103A. However, since the material of the pillar bump 103 is, in general, very robust, and typically has a stiffness that exceeds that of at least some of the materials that make up the semiconductor chip 102—and in particular, the dielectric materials included in the metallization system 104—relatively little deformation energy will be absorbed by plastic deformation of the pillar bump 103A during the chip packaging thermal interaction. Instead, the majority of the loads 103S, 103T and 103M will be translated through the pillar bump 103A and into the metallization layers, such as layers 104A-104C, underlying the pillar bump 103A. These translated loads will generally have the highest magnitude in an area of the metallization system 104 that is below the edges 113 (shown in FIG. 1d as a dotted line) of the pillar bump 103A.

Under the conditions outlined above, highly localized stresses may develop in one or more of the metallization layers of the metallization system 104, such as a tensile stress 108T on one side of the pillar bump 103A and a compressive stress 108C on the opposite side of the pillar bump 103A. Furthermore, if the stresses 108T and/or 108C are of a high enough magnitude, a local failure of one or more of the metallization layers may occur below the pillar bump 103A. Typically, a failure of a given metallization layer having a substantially homogeneous material system will manifest as a delamination or a crack 109, and will normally occur where the loads are highest—i.e., near the edges 113 of the pillar bump 103A, as shown in FIG. 1d. In other cases, such as those utilizing a substantially inhomogeneous material system having locally varying fracture energies, the crack 109 may only occur in a single metallization layer, such as the layer 104C shown in FIG. 1d, whereas in other cases, and depending on many factors, the crack 109 may propagate either deeper or shallower into the underlying metallization system 104, e.g., spreading from one metallization layer to another.

Delamination failures and cracks, such as the crack 108, that may occur in a metallization layer below a pillar bump, such as the pillar bump 103A shown in FIG. 1d, are sometimes subject to premature failure, as the crack 108 may prevent the pillar bump 103A from making a good electrical connection to the contact structure 107 therebelow. However, since the delamination/crack defects described above do not occur until the chip packaging assembly stage of semiconductor chip manufacture, the defects will generally not be detectable until a final quality inspection is performed. In some cases, after the flip-chip operation has been completed, the chip package 100 may be subjected to acoustic testing, such as C-mode acoustic microscopy (CSAM). Cracks 109 that may be present in the metallization system 104 of the semiconductor chip 102 below the pillar bumps 103 will have a characteristic appearance during the CSAM inspection process that is recognizably different from that of pillar bumps 103 that do not have such cracks 109 therebelow. Such pillar bumps are sometimes referred to as "white bumps," "white spots," or "ghost bumps," since this is how the difference in the acoustic signal in the CSAM images was first visualized. White bump defects may impose a costly downside to the overall chip manufacturing process, as they do not occur, and hence cannot be detected, until a significant material and manufacturing investment in the chip has already occurred. Furthermore, in those instances where the assembled chip package 100 is not subjected to CSAM inspection, undetected white bump defects may lead to reduced overall device reliability.

Additionally, the development and use of dielectric materials having a dielectric constant (or k-value) of approximately 3.5 or lower—which are often referred to as "low-k dielectric materials"—has led to an increased incidence of white bumps. Typically, low-k dielectric materials have lower mechanical strength, mechanical modulus, and adhesion strength than do some of the more commonly used dielectric materials having higher k-values, such as silicon dioxide, silicon nitride, silicon oxynitride, and the like. As metallization systems utilize more, and sometimes thicker, metallization layers that are made up of low-k dielectric materials, there is a greater likelihood that the lower strength low-k materials will rupture when exposed to the loads that are imposed on the metallization layers underlying the pillar bumps, thus leading to delaminations and cracks—i.e., white bump defects. In particular, cracks tend to occur, or at least initiate, in the low-k metallization layers that are closest to the upper surface of the a semiconductor chip—i.e., closest to the last metallization layer—as the deformation energy is typically greatest near the upper surface, while in many cases decreasing in lower metallization levels. Furthermore, it appears that the type of white bump problems described above may sometimes even be further exacerbated in metallization layers comprised of ultra-low-k (ULK) materials having k-values of approximately 2.7 or lower, which in some cases may have even lower-strength mechanical properties than that of some low-k materials.

In some prior art semiconductor chips, the detrimental effects associated with white bump defects can sometimes be minimized by reducing the number of critical and/or sensitive circuit elements that are positioned in those areas of a metallization system that are below and/or adjacent to pillar bumps that are formed in those regions of a chip where white bumps are more likely to occur. For example, the size of a body—i.e., its length or width—is one factor that may have a significant influence on the total amount of thermal expansion that body undergoes when exposed to an elevated temperature. As such, the points of greatest thermal interaction—and commensurately highest out-of-plane loads—may occur in those areas of the semiconductor chip which are farthest from a neutral center, or centerline, of the chip, such as the periphery of the chip, such as the periphery 102P and in particular, those areas near the corners 102E of the chip (see, e.g., FIG. 1*c*). Accordingly, during the design and layout of a given semiconductor chip, it is sometimes feasible to position critical circuit elements and to route at least some conductive elements away from those areas of the chip that are typically exposed to greatest amount of differential thermal expansion between the semiconductor chip and the carrier substrate, e.g., near the edges and corners of the chip.

However, simply adjusting the layout of the various circuit elements as described above does not always address all of the problems that may often be related to white bumps, which can sometimes occur in regions of a semiconductor chip that would not normally be associated with the highest thermal interaction and out-of-plane loads. For example, in some cases, a certain area of a particular low-k or ULK material layer of a given back-end-of-line (BEOL) metallization system may display mechanical properties that are uncharacteristically lower than may normally be expected of that specific material. Such lower mechanical properties may be due to any one of several different factors, including variation and/or drifting in the material deposition parameters, cleanliness, contamination, and/or microscratching issues associated with a given tool or wafer, and the like. Furthermore, such adjusted layout configurations often tend to give up valuable chip real estate, which can sometimes limit the type of applications for which the resulting chips may be used.

Accordingly, and in view of the foregoing, there is a need to implement new strategies to address the design and manufacturing issues associated with the detrimental effects that white bump occurrences can often have on a semiconductor chip during the typical chip packaging operations. The present disclosure relates to various testing methods and mitigation strategies that are directed to avoiding, or at least minimizing, the effects of one or more of the problems identified above.

SUMMARY OF THE DISCLOSURE

The following presents a simplified summary of the present disclosure in order to provide a basic understanding of some aspects disclosed herein. This summary is not an exhaustive overview of the disclosure, nor is it intended to identify key or critical elements of the subject matter disclosed here. Its sole purpose is to present some concepts in a simplified form as a prelude to the more detailed description that is discussed later.

Generally, the subject matter disclosed herein relates to detecting the presence of anomalous weak BEOL sites in a metallization system of a semiconductor chip or wafer. One illustrative method disclosed herein includes, among other things, performing a lateral force test on a pillar bump formed above a metallization system of a semiconductor chip, the lateral force test including contacting the pillar bump with a test probe while moving the test probe at a substantially constant speed that is less than approximately 1 µm/sec along a path that is oriented at a substantially non-zero angle relative to a plane of the metallization system. Furthermore, the substantially non-zero angle is established so that the test probe is moving substantially away from the metallization system and so that a force imposed on said pillar bump by the test probe during the lateral force test has an upward component that induces a tensile load on the metallization system. Moreover, the disclosed method also includes determining a behavioral interaction between the pillar bump and the metallization system during the lateral force test.

Another illustrative embodiment of the present disclosure is a method that includes generating a comparative behavioral interaction curve for a representative pillar bump formed above a representative metallization system of a representative semiconductor chip. The disclosed method further includes, among other things, performing a first lateral force test on a first pillar bump formed above a metallization system of a semiconductor chip, the first lateral force test including contacting the first pillar bump with a test probe while moving the test probe at a substantially constant speed that is less than approximately 0.1 µm/sec along a path that is oriented at a substantially non-zero angle relative to a plane of said metallization system. Furthermore, the substantially non-zero angle is established so that the test probe is moving substantially away from the metallization system and so that a force imposed on the first pillar bump by the test probe during the first lateral force test has an upward component that induces a tensile load on the metallization system. Finally, the illustrative method includes determining a first behavioral interaction between the first pillar bump and the metallization system during the first lateral force test, and comparing the first behavioral interaction to the comparative behavioral interaction curve.

Also disclosed herein is a device that includes, among other things, a plurality of pillar bumps formed above a metallization system of a semiconductor chip, and at least one notch formed in a side of each of the plurality of pillar bumps, wherein the at least one notch is a substantially asymmetrically shaped notch.

BRIEF DESCRIPTION OF THE DRAWINGS

The disclosure may be understood by reference to the following description taken in conjunction with the accompanying drawings, in which like reference numerals identify like elements, and in which:

FIGS. 7a-7e schematically show various views of an illustrative system and method that may be used to repair anomalous stiff pillar bumps in accordance with some embodiments of the present disclosure;

FIGS. 9c-9l schematically depicts various embodiments of illustrative test probe tips that may be used for testing pillar bumps in accordance with one or more of the testing configurations illustrated in FIGS. 9a and 9b.

Figure 1A:
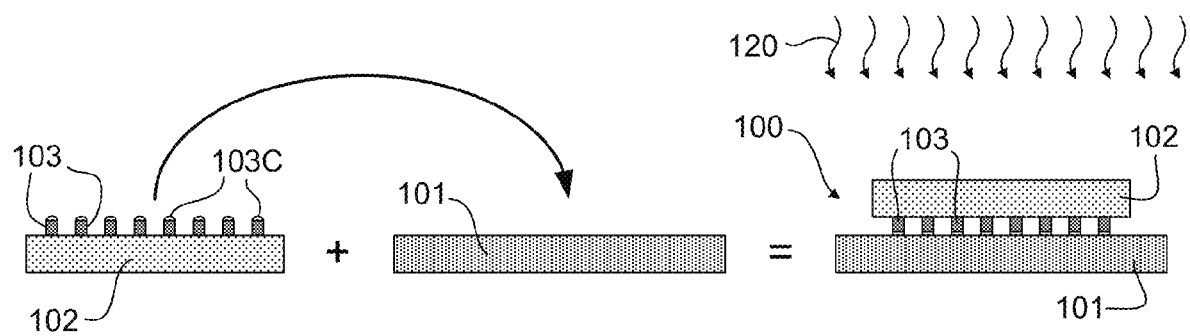
FIGS. 1a-1b schematically illustrate a flip-chip packaging operation of a prior art semiconductor chip and a carrier substrate.
Figure 1B:
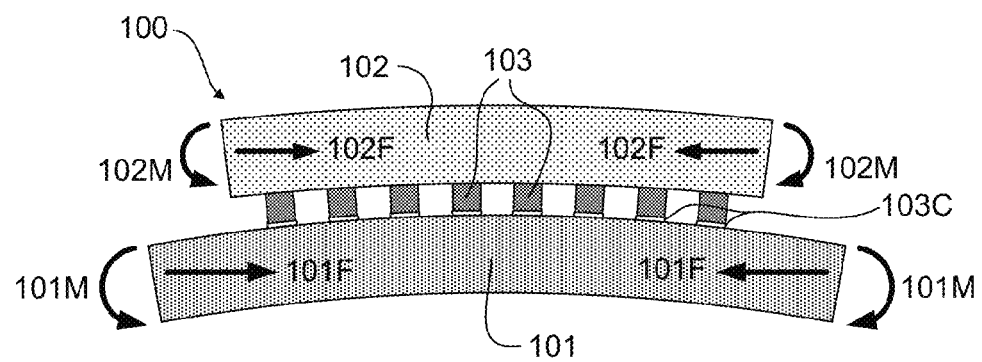

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the present subject matter are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the subject matter of the present disclosure is directed to various methods and systems that may be employed to test and evaluate the metallization layers of a so-called back-end-of-line (BEOL) metallization system and the pillar bumps that may be formed thereabove. In certain embodiments disclosed herein, lateral force tests may be performed on each of a plurality of pillar bumps formed above a representative BEOL metallization system so as to simulate the type of out-of-plane loads that may be imposed on the pillar bumps as a result of chip packaging thermal interaction during a flip-chip assembly process. For example, each lateral force test may be performed until a failure occurs in the metallization layers underlying the tested pillar bump, e.g., until a crack is induced. In some embodiments, the crack may be representative of the type of crack failures that occur as a result of thermal interaction during chip packaging, such as the crack 109 shown in FIG. 1d. Furthermore, relevant testing data may be gathered during the lateral force tests, and thereafter evaluated so as to determine the behavioral interaction between the pillar bumps and the underlying metallization layers when exposed to loads such as those that may be generated during flip-chip assembly. From this, a statistical assessment may be performed so as to establish a typical behavioral interaction curve for a given pillar bump/metallization system configuration that may be indicative of how that configuration would normally be expected to react when exposed to out-of-plane loads.

In at least some embodiments of the present disclosure, a typical behavioral interaction curve for a given pillar bump/metallization system configuration may be used in a comparative fashion for a variety of evaluation purposes when testing additional products that may be formed based on similar configuration parameters. For example, in certain embodiments a behavioral interaction curve may be used to locate and characterize processing and/or material-related issues that may be associated with anomalous pillar bumps and/or the underlying metallization layers. In other embodiments, a typical behavioral interaction curve may be used to evaluate the overall robustness of a given chip design and layout, which may be influenced by parameters such as: number of metallization layers; dielectric material types, strengths and thicknesses; size, configuration and relative positioning of conductive elements; and/or size, configuration and positioning of pillar bumps relative to underlying features. In still other embodiments, a behavioral interaction curve may also be used as a quality assurance tool to evaluate tool performance and/or drift (i.e., changes in materials or deposition parameters) in the processes that may be used to form low-k dielectric materials, ultra-low k (ULK) dielectric materials, and/or pillar bumps. In yet further embodiments, a typical behavioral interaction curve may also be used to evaluate new materials for advanced device generations, such low-k and/or ULK dielectric materials, which may have substantially reduced mechanical strength, and therefore be more susceptible to thermal interaction induced crack-like failures.

It should be understood that, unless otherwise specifically indicated, any relative positional or directional terms that may be used in the descriptions below—such as "upper," "lower," "on," "adjacent to," "above," "below," "over," "under," "top," "bottom," "vertical," "horizontal," and the like—should be construed in light of that term's normal and everyday meaning relative to the depiction of the components or elements in the referenced figures. For example, referring to the schematic cross-section of the semiconductor chip 102 depicted in FIG. 1d, it should be understood that the passivation layer 106 is formed "above" the last metallization layer 104A, and the conductive bond pad 105 is positioned "below" or "under" the pillar bump 103A. Similarly, it should also be noted that the passivation layer 106 may be positioned "on" the last metallization layer 104A in those embodiments wherein no other layers or structures are interposed therebetween.

Figure 1C:
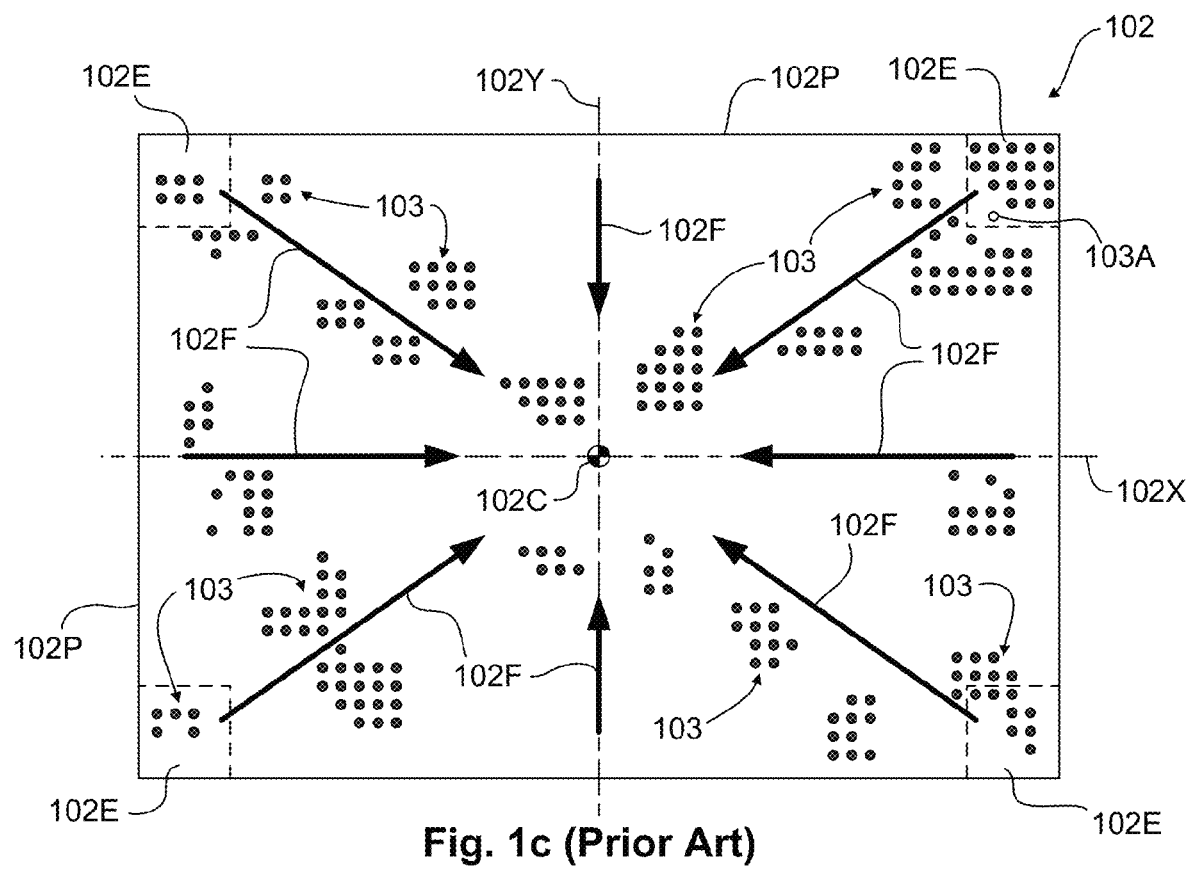
FIG. 1c schematically illustrates a plan view of the prior art semiconductor chip of FIGS. 1a-1b.
Figure 1D:
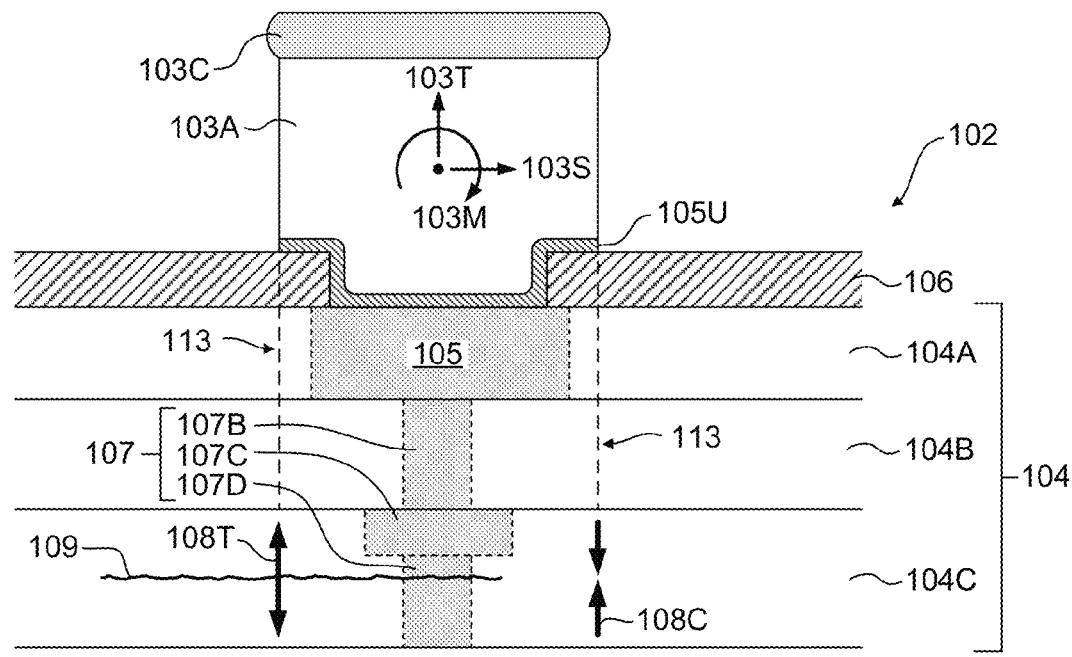
FIG. 1d schematically illustrates out-of-plane loading on a representative pillar bump and underlying metallization system of a prior art semiconductor chip after the flip-chip packaging operation of FIGS. 1a-1b.
Figure 2:
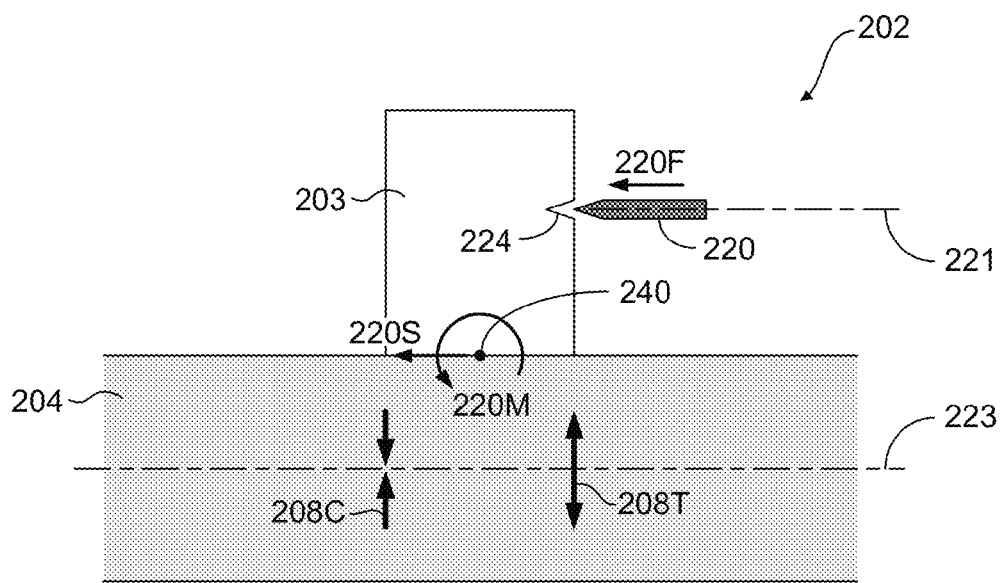
FIG. 2 schematically depicts an illustrative test configuration disclosed herein that may be used for lateral force testing of pillar bumps formed above a metallization system of a semiconductor chip or wafer.

FIG. 2 schematically depicts one illustrative embodiment of a novel test configuration that may be used for testing the behavioral interaction between a representative pillar bump 203 and an underlying metallization system 204 of a wafer or semiconductor chip 202. As shown in FIG. 2, the pillar bump 203 may be formed above the metallization system 204, which may include a plurality of metallization layers and conductive features, such as bond pads, contact vias and conductive lines, which for simplicity are not illustrated in FIG. 2. See, e.g., FIG. 1d, described in additional detail above. In some embodiments, the pillar bump 203 may be made up of any one of a number of well-known and highly conductive metals, such as copper, gold, silver and the like, or alloys thereof. Furthermore, it should be appreciated that the pillar bump 203 may represent one of a plurality of pillar bumps that are each formed above and generally distributed over an upper surface of the semiconductor chip 202, some of which may be tested so as to established a typical behavioral interaction curve, as will be described in further detail below.

As noted above, the metallization system 204 may include a plurality of various metallization layers (not shown), each of which may be made up of one or more respective dielectric materials, and include a plurality of conductive features (not shown), such as contract vias and/or conductive lines and the like, which may be positioned and arranged within each of the various metallization layers as may be required to define an overall circuit layout of the semiconductor chip 202. Depending on the specific design of the semiconductor chip 202, one or more of the respective metallization layers may include a low-k and/or ULK dielectric material.

In accordance with the presently disclosed subject matter, the behavioral interaction of the pillar bump 203 and the metallization system 204 may be tested and evaluated using a lateral force test. In certain illustrative embodiments, a test probe 220 may be moved at a constant speed along a path 221 that is substantially parallel to the plane 223 of the metallization system 204 so as to contact the pillar bump 203. When the test probe 220 contacts the pillar bump 203, an indentation or notch 224 may be formed in the pillar bump 203 as the test probe 220 continues to move at a constant speed and pushes on the pillar bump 203. As a result of the constant speed movement of the test probe 220, a force 220F is imposed on the pillar bump 203, which can be measured and recorded over the duration of the test. In some embodiments, the resulting force 220F imposed on the pillar bump 203 by the test probe 220 may approximately represent the type of loading that is sometimes induced on a given pillar bump during the thermal interaction of flip-chip packaging. Furthermore, the force 220F on the pillar bump 203 may in turn induce a shear load 220S and an overturning moment 220M at an interface 240 between the pillar bump 203 and the metallization system 204, thereby resulting in localized tensile and compressive stresses 208T and 208C in the metallization system 204 in substantially the same manner as previously described above with respect to the pillar bump 103A shown in FIG. 1d, thereby approximating a stress field in the metallization system 204 that can result in white bump occurrences.

In some exemplary embodiments of the present disclosure, the lateral force test described above may be continued on the pillar bump 203 until a load and/or displacement induced failure occurs proximate to the pillar bump 203 in the underlying metallization system 204—e.g., until a crack occurs in one or more of the metallization layers (not shown) of the metallization system 204, such as the crack 109 described and illustrated with respect to FIG. 1d above. Additionally, test data related to the resulting force 220F and the total distance moved by the probe 220 throughout the duration of the lateral force test may be recorded, which may then be used to generate a behavioral interaction curve for the tested pillar bump 203 and metallization system 204. Furthermore, additional lateral force tests may be performed on each of a plurality of other similarly configured pillar bumps, which may then be used to create a typical behavioral interaction curve for a given pillar bump and metallization system configuration, examples of which are illustrated in FIG. 3 and described below.

Figure 3:
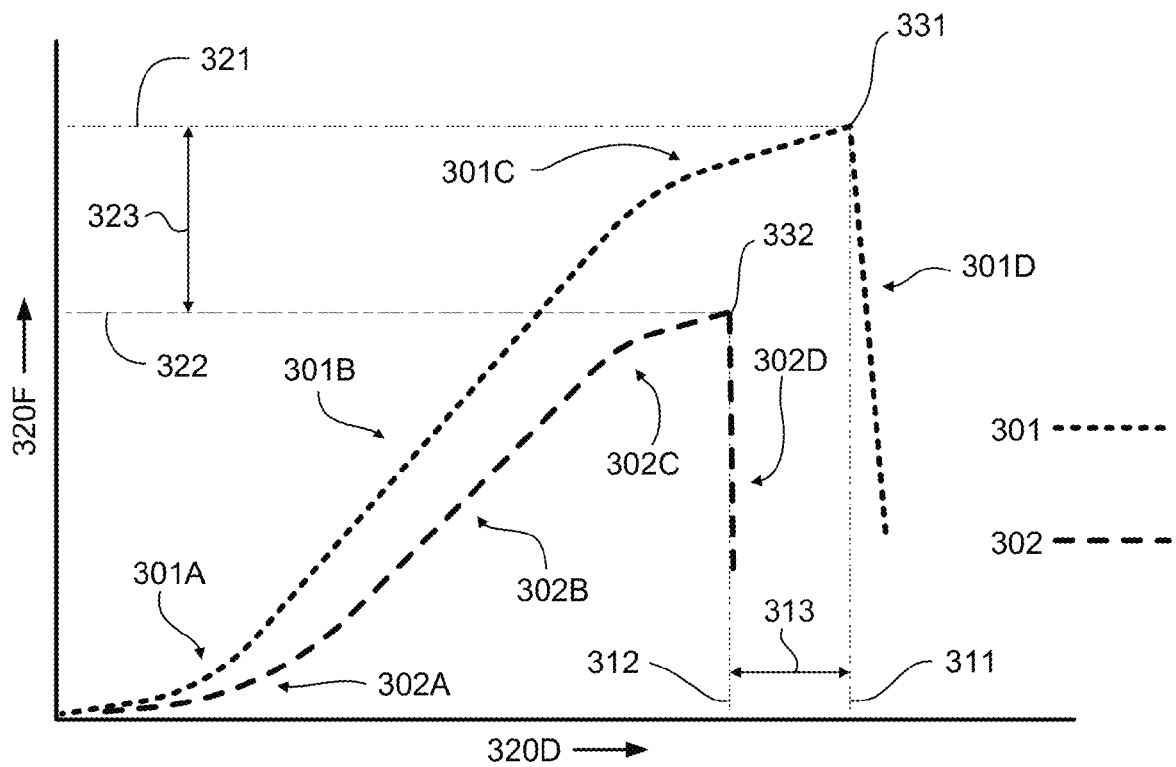
FIG. 3 graphically illustrates comparative curves representing the behavioral interaction between pillar bumps and an underlying metallization system of a semiconductor chip or wafer when tested to crack failure using fast-speed and slow-speed lateral force tests and the illustrative test configuration of FIG. 2 disclosed herein.

FIG. 3 graphically depicts typical force/distance behavioral interaction curves that represent data obtained during lateral force testing of a plurality of pillar bumps formed above a metallization system of a semiconductor chip or wafer when tested to crack failure using the illustrative test configuration of FIG. 2, as described above. As shown in FIG. 3, both of the force/distance curves 301 and 302 essentially plot a distance 320D that is traveled by a test probe (such as the test probe 220 of FIG. 2) against a force 320F that is generated by the test probe on a representative typical pillar bump (such as the pillar bump 203 of FIG. 2) throughout the duration of a lateral force test. However, curve 301 represents test data that is obtained by moving the test probe at a constant speed during the lateral force tests that is different than the constant test probe speed used to generate curve 302, as will be further described below.

As may be known by those having ordinary skill in the art, a constant test probe speed that is greater than approximately 1 μm/sec (micrometers, or microns, per second) and ranging up to as high as about 10 μm/sec has been used in prior art test schemes to evaluate the behavior of at least some pillar bump/metallization system configurations. The force/distance curve 301 represents a typical behavioral interaction of a given pillar bump/metallization system that has been tested using such a known constant test probe speed, i.e., ranging from approximately 1-10 μm/sec. The force/distance curve 302, on the other hand, represents a typical behavioral interaction of a pillar bump/metallization system having a substantially similar configuration as that used to generate the fast speed test curve 301, wherein however the lateral force tests have been performed using a much slower constant probe speed. More specifically, the force/distance curve 302 may be based on a constant test probe speed that is less than the typical minimum prior art test probe speed of approximately 1 μm/sec, and in certain embodiments may even be less than approximately 0.1 μm/sec—or about 10-100 times slower than the typical prior art lateral force test. For comparative purposes, a lateral force test that is performed in the range of approximately 1-10 μm/sec (e.g., the tests represented by curve 301) is hereinafter referred to as a "fast speed test," wherein a test that may be performed at less than approximately 0.1 μm/sec (e.g., the tests represented by curve 302) is hereinafter referred to as a "slow speed test." Accordingly, it should be appreciated that a slow speed test may be performed at a constant test probe speed that may be at least 1 to 2 orders of magnitude slower, i.e., at least 10 to 100 times slower, than that of a typical fast speed test.

The fast speed curve 301 can generally be characterized as having four distinct response regions: 301A, 301B, 301C and 301D. The first region 301A of curve 301 illustrates the initial behavioral response of the pillar bump/metallization system immediately after the pillar bump has been contacted by the lateral force test probe. As illustrated in FIG. 3, the first region 301A shows a substantially non-linear force/distance response, wherein the distance 320D (horizontal axis of the FIG. 3 graph) traveled by the test probe increases at a greater rate than the force 320F (vertical axis of the FIG. 3 graph) imposed on the pillar bump by the test probe, which may be the result of some degree of strain hardening of the pillar bump during the initial bump deformation.

The second region 301B of curve 301 illustrates a substantially linear force/distance response, during which time the distance 320D traveled by the test probe and the force 320F imposed on the pillar bump both increase at a substantially constant rate. Thereafter, as illustrated by the third region 301C, the force/distance response of the pillar bump/metallization system again displays a substantially non-linear characteristic, which may be indicative of an acceleration of the microcracking failure that is occurring in the low-k and/or ULK dielectric materials making up the metallization system. Accordingly, the distance 320D traveled by the test probe once again increases at a greater rate than the force 320F imposed on the pillar bump as both the force 320F and the distance 320D traveled both move toward creating an eventual macroscopic crack failure, indicated by point 331.

The fourth region 301D of curve 301 illustrates the behavioral response of the pillar bump/metallization system to the fast speed test after crack failure at point 331 has occurred. The post-crack force/distance response illustrated by the fourth region 301D may also be characterized as being substantially linear in nature, wherein the force 320F on the pillar bump drops quickly as the crack widens and propagates through the metallization system. As shown in FIG. 3, the crack point 331 occurs after a force 320F having a magnitude 321 has been imposed on the pillar bump, and the test probe has traveled a total distance 320D of magnitude 311.

As shown in FIG. 3, the force/distance curve 302, which represents the behavioral interaction of the pillar bump/metallization system when exposed to the slow speed test disclosed herein, has a similar overall configuration as the fast speed curve 301, and furthermore displays similarly characterized curve regions 302A, 302B, 302C and 302D. More specifically, the first region 302A of curve 302 is substantially non-linear, indicating that the distance 320D traveled by the test probe increases at a greater rate than the force 320F imposed on the pillar bump. The second region 302B shows a substantially linear force/distance response such that both the distance 320D and force 320F increase at relatively constant rates, whereas the third region 302C is again non-linear, as is the case with the third region 301C of the fast test curve 301. After a crack has occurred (identified as point 332), the post-crack fourth region 302D of the slow speed curve 302 again displays a substantially linear characteristic, wherein the force 320F on the pillar bump drops precipitously versus the distance 320D traveled by the test probe as the crack widens as propagates through metallization system.

It should be noted, however, that while the general configuration and characteristics of the various regions of the fast speed and slow speed test curves 301 and 302 have a substantially similar shape and appearance, test curve 302 indicates that a crack will occur at both a lower force 320F and a shorter distance 320D traveled during the slow speed lateral force tests (represented by curve 302), as disclosed herein, when compared to the fast speed tests (represented by curve 301).

More specifically, a crack occurs during the slow speed tests of curve 302 (see, crack point 332) after a force 320F having a magnitude 322 has been imposed on the pillar bump. As shown in FIG. 3, the force 322 is less by an amount 323 than the force 321 necessary to create a crack during the fast speed tests of curve 301 (see, crack point 331). In one example, the force 322 may be approximately 10-35% less than the force 321.

Similarly, the slow speed tests of curve 302 show that the total distance 320D traveled by the test probe during prior to the initiation of a crack has a magnitude 312, which is less by an amount 313 than the corresponding distance 311 needed to create a crack during the fast speed tests of curve 301. In one example, the distance 312 may be about 5-30% less than the distance 311. Accordingly, when used as a predictive and/or comparative tool for evaluating data associated with lateral force tests that may be performed on similar pillar bump/metallization system configurations, the fast speed test curve 301 would indicate that a given system configuration may generally be more robust, i.e., able to resist higher loads and/or greater lateral movement during chip packaging interaction, than would be indicated by the slow speed test curve 302. However, at least some qualitative and quantitative evidence indicates that slow speed tests may be more a representative predictor of crack-related product failures in actual flip-chip packages, as will be discussed in further detail below.

Figure 4A:
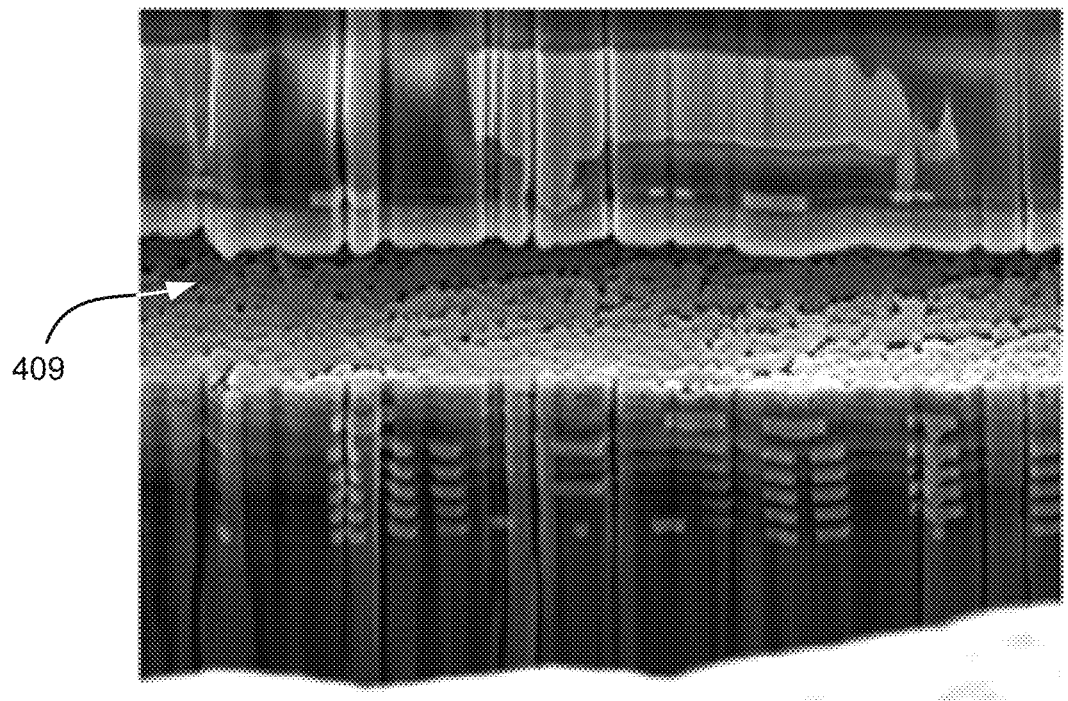
FIGS. 4a-4b are photomicrographs showing crack morphology of cracks in the metallization systems of representative semiconductor chips that occurred as a result of a flip-chip bonding operation.
Figure 4B:
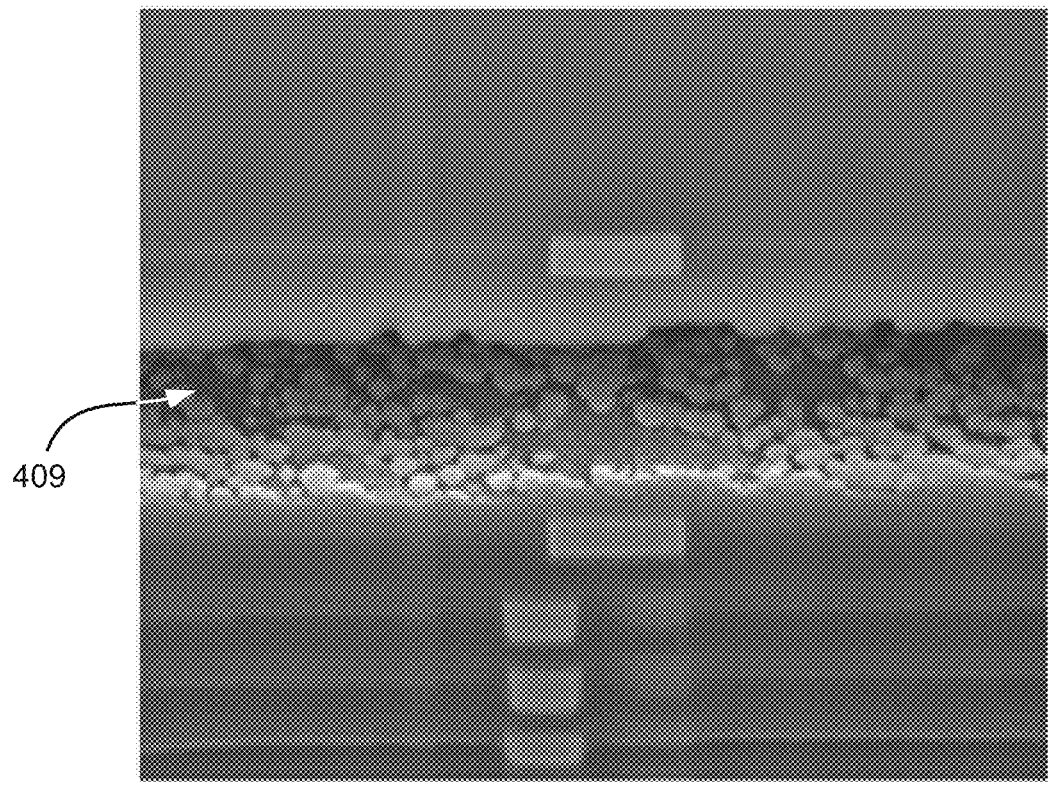
Figure 4C:
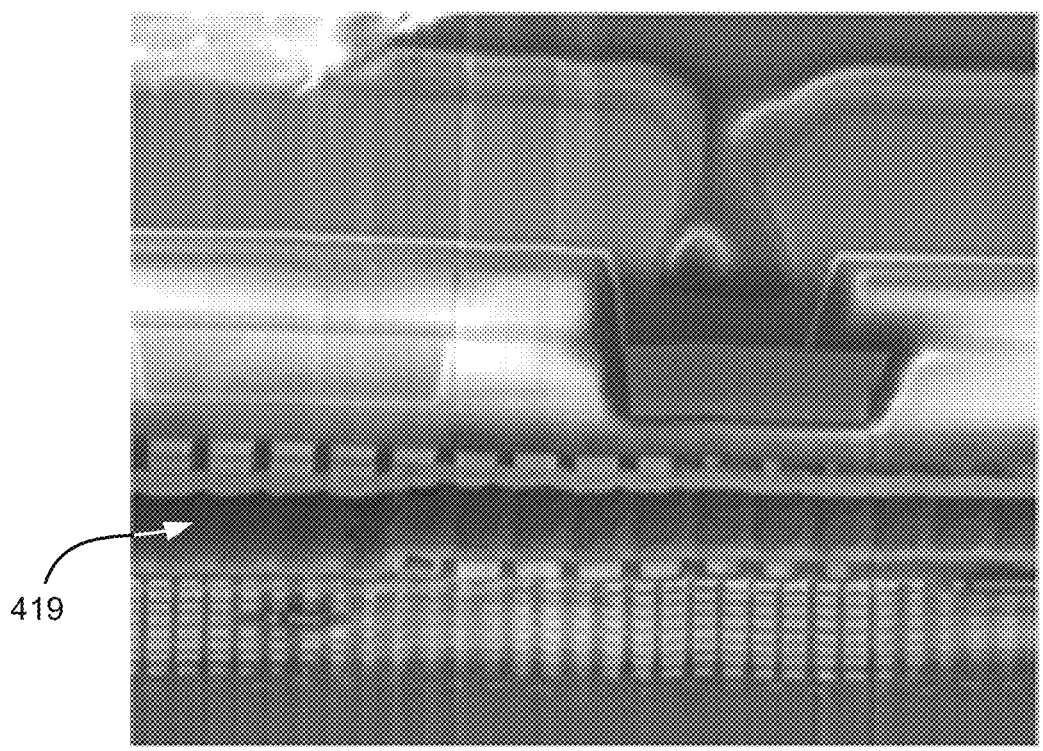
FIGS. 4c-4d are photomicrographs showing the crack morphology of cracks in the metallization systems of representative semiconductor chips that occurred as a result of a slow-speed bump test to crack failure using the illustrative testing configuration of FIG. 2 disclosed herein.
Figure 4D:
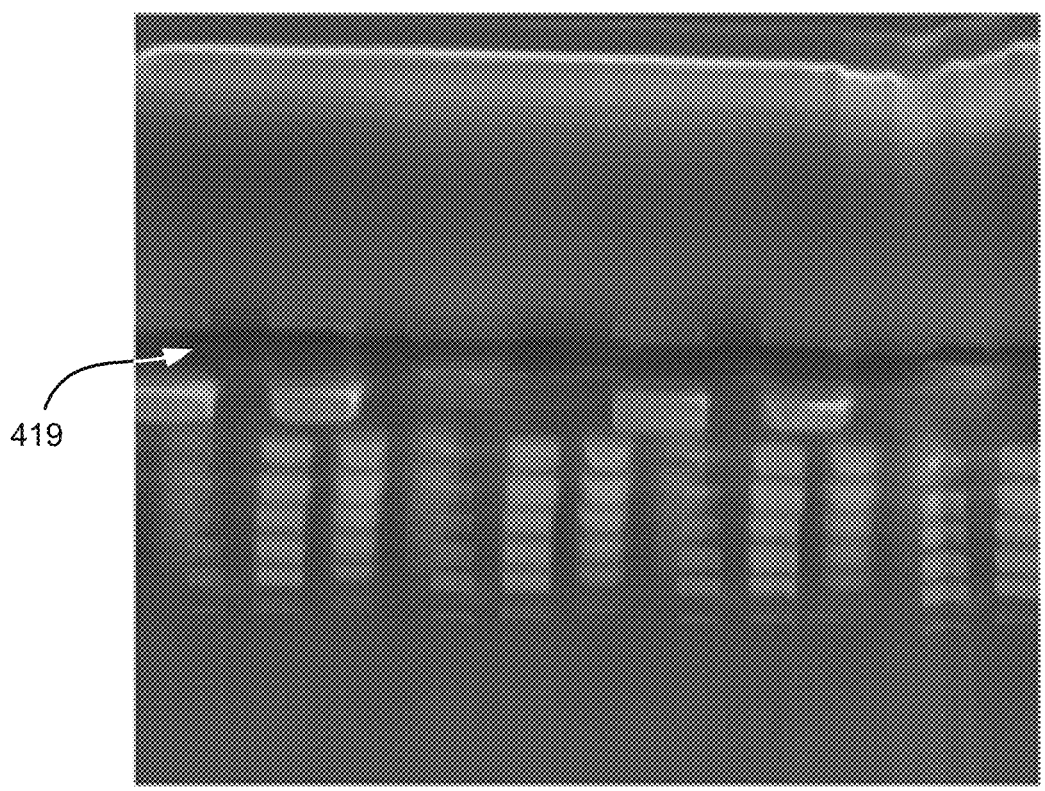
Figure 4E:
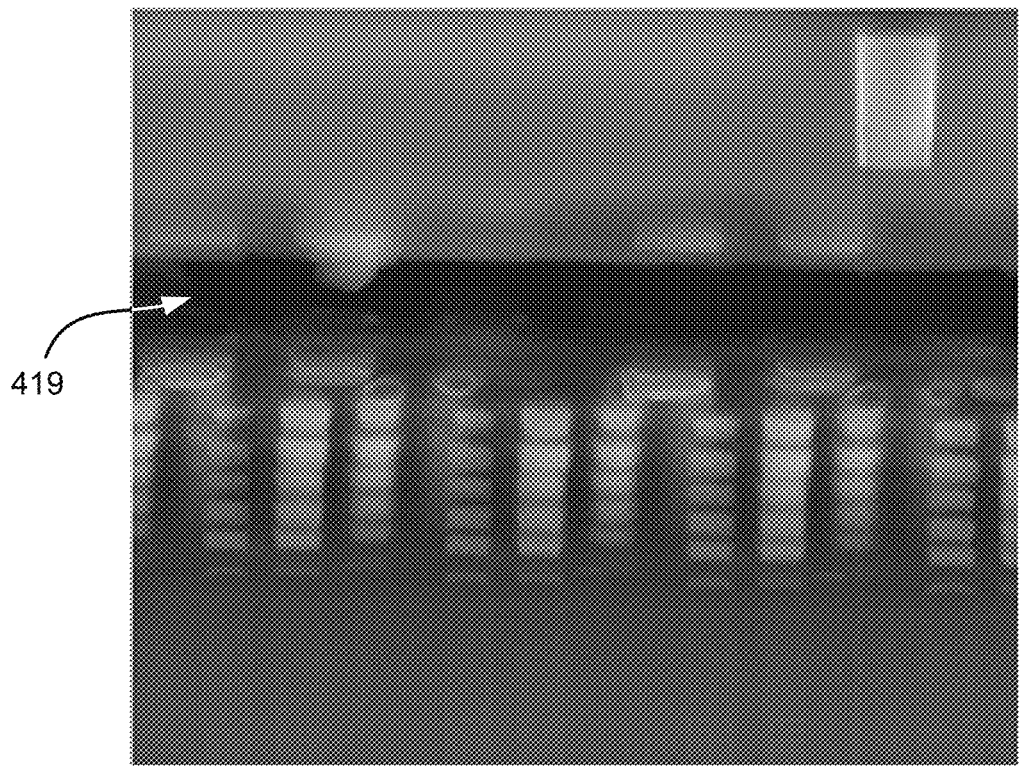
FIGS. 4e-4h are photomicrographs showing the crack morphology of cracks in the metallization systems of representative semiconductor chips that occurred as a result of a fast-speed bump test to crack failure using the illustrative testing configuration of FIG. 2 disclosed herein.
Figure 4F:
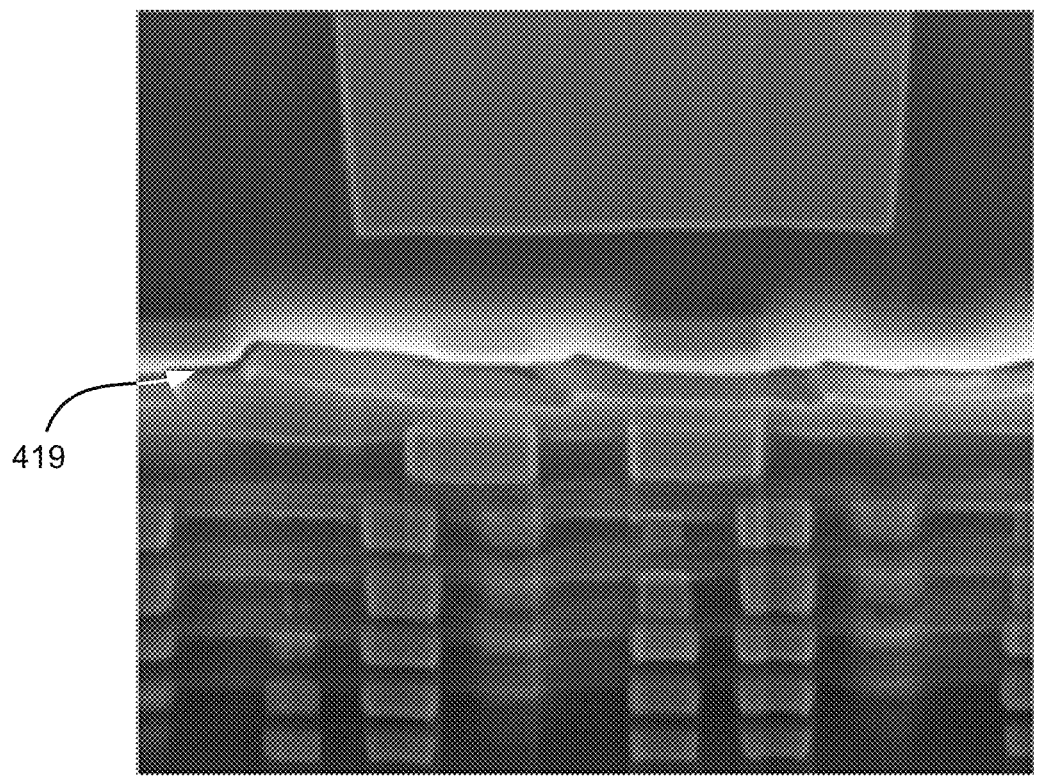

FIGS. 4a-4h are scanning electron microscope (SEM) photographs of illustrative crack failures in BEOL metallization layers below the pillar bumps of various representative semiconductor chips. More specifically, FIGS. 4a and 4b are SEM photographs of actual product cracks 409 that have occurred during a typical flip-chip bonding and assembly process. As shown in FIGS. 4a and 4b, the cracks 409 display a substantially grainy or pebbly morphology, which is often typical of the appearance of the type of cracks that occur as a result of the thermal interaction between the semiconductor chip and a carrier package substrate, as previously described.

FIGS. 4c-4f are SEM photographs of illustrative cracks 419 in the BEOL metallization layers below pillar bumps of representative semiconductor chips that have been created during fast speed lateral force tests, such as those represented by test curve 301 shown in FIG. 3 and described above. As can be seen in FIGS. 4c-4f, the cracks 419 created during fast speed lateral force tests display a substantially smooth crack morphology, which is significantly different from the pebbly crack morphology seen in the cracks 409 that have occurred in actual semiconductor chips during flip-chip assembly. This difference in crack morphology between the cracks 409 induced in actual failed products and the cracks 419 created during fast speed lateral force tests provides at least some evidence that the fast speed test cracks 419 may not accurately represent the real-world conditions that occur during the flip-chip bonding and assembly process that lead to the initiation and propagation of white bump cracks in actual products, such as the illustrative cracks 409 shown in FIGS. 4a and 4b.

Figure 4G:
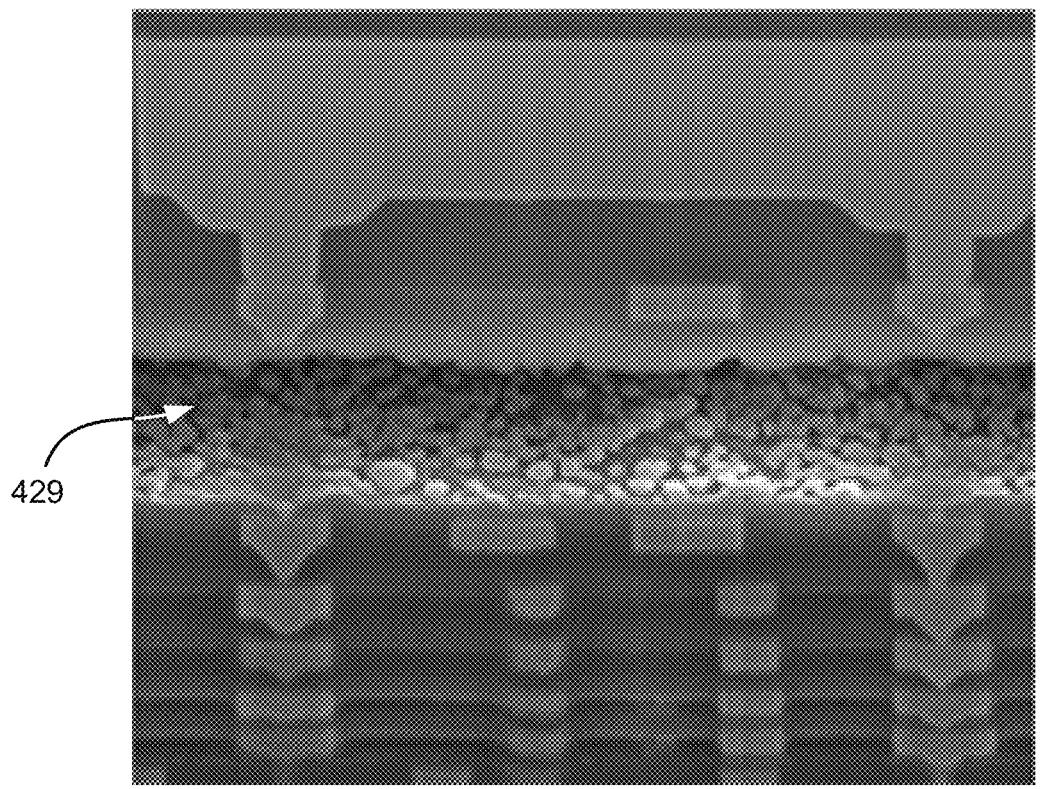
Figure 4H:
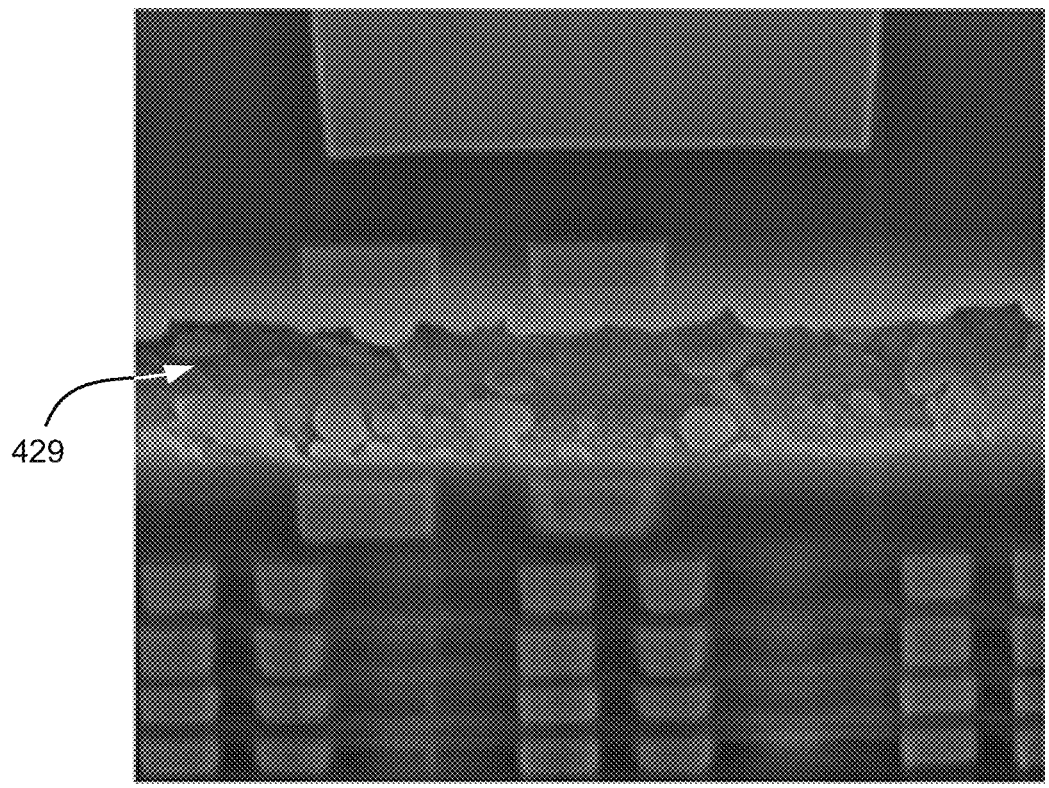

On the other hand, FIGS. 4g and 4h are SEM photographs showing cracks 429 that have been created in the BEOL metallization layers of representative semiconductor chips during a slow speed lateral force test disclosed herein, such as the tests represented by the curve 302 shown in FIG. 3. As shown in FIGS. 4g and 4h, the cracks 429 display a substantially grainy or pebbly appearance—i.e., a morphology that is substantially similar to the morphology of the bonding and assembly-related cracks 409 seen in actual real-world products, as illustrated in FIGS. 4a and 4b. This similarity in crack morphology may indicate that slow speed lateral force tests disclosed herein more accurately represent the conditions that arise in actual semiconductor chips during the flip-chip process, as compared to the fast speed tests lateral force tests previously described, which may result in the substantially smoother crack morphology seen in FIGS. 4c-4f. Additionally, strain rate calculations that are performed on actual products during the reflow process in the regime where crack failures would typically be expected to initiate in the BEOL metallization layers indicate that the rate of strain during reflow is slower than that which occurs during a typical fast speed lateral force test, yet provides reasonably good correlation to the rate of strain that occurs during slow speed tests.

As noted above, lateral force tests using a constant test probe speed in the range of approximately 1-10 µm/sec—i.e., fast speed tests—have generally been performed in prior art testing schemes when evaluating and characterizing the behavioral interaction of pillar bumps with their underlying metallization systems. Furthermore, as may be appreciated by a person of ordinary skill in the art after a complete reading of the present disclosure, the amount of time that is required to perform fast speed lateral force tests is much shorter than the amount of time that may be required to perform the corresponding slow speed tests—each of which may take as much as 10 to 100 times longer to perform, since the constant test probe speed used during the slow speed tests disclosed herein is less than 0.1 µm/sec. When hundreds, or even thousands, of lateral force tests are performed so as to characterize the behavioral interaction of a given pillar bump/metallization system configuration, and hundreds or even thousands more tests are performed during chip quality assurance assessments, or to evaluate different dielectric materials or chip configurations, use of the typical fast speed test may result in an overall reduction in the amount of time needed to perform a given set of tests. However, in many instances, the perceived economic benefits that may be associated with the reduced amount of time used to perform the prior art fast speed tests is significantly outweighed by the additional correlational accuracy provided by the novel slow speed tests of the present disclosure. Thus, contrary to traditional manufacturing and inspection operations, where manufacturers are constantly pressured to perform operations faster so as to reduce cost, by performing the more time-consuming slow speed test disclosed herein, unexpected benefits may be achieved.

As the above discussion shows, fast speed lateral force testing is generally not as representative of real-world chip packaging interaction effects as are the novel slow speed testing methods disclosed herein. For example, the fast speed tests may give a misleading impression that a given pillar bump/metallization system configuration can withstand a higher load prior to crack initiation than it may actually be capable of resisting. Accordingly, when a typical behavioral response curve is generated using prior art fast speed lateral force tests, such as the test curve 301 of FIG. 3 above, and that typical behavioral response curve is used to perform an evaluation of a specific semiconductor chip BEOL metallization system layout, the fast speed test curve may indicate that the chip layout is more robust under chip packaging thermal interaction forces than it actually is. As such, an overly optimistic design margin may be attributed to the design when in fact the design margins may be significantly lower, or even completely nonexistent. In such cases, force/distance behavioral interaction curves that are based on the novel slow speed lateral force tests disclosed herein may be substantially more accurate, thus providing the requisite design margins, as well as fostering a greater overall reliability in the chip evaluation process.

In some illustrative embodiments of the present disclosure, a typical force/distance behavioral interaction curve, such as the curve 302 of FIG. 3, may be used in a comparative fashion in conjunction with additional lateral force testing to evaluate and characterize atypical, or anomalous, behavioral interactions between a given BEOL metallization system configuration and the pillar bumps formed thereabove. For example, random statistical testing may be performed on a plurality of pillar bumps formed above a metallization system of a semiconductor chip or wafer using the slow speed testing techniques described herein. In certain embodiments, the force/distance curves generated for some specific tests may display an unexpectedly different response to the lateral force test than might otherwise have been predicted by the typical behavioral interaction curve for a similarly configured pillar bump/metallization system. This is turn may thereby indicate the presence of one or more material, configuration, and/or design related anomalies, which may be associated either with the pillar bump, the underlying metallization system, or some combination thereof, as will be described in further detail below.

In some instances, one or more of the BEOL metallization layers making up a given metallization system may be abnormally and/or unexpectedly weaker than would normally be anticipated for a typical system having a similar configuration. Such weak areas within the metallization system may be attributable to any one or more of several different factors, including a drift in process deposition parameters, processing tool malfunction and/or cleanliness, substrate cleanliness, bonding or adhesion issues between adjacent layers and/or conductive elements, and the like. In other cases, anomalous weak areas in a given BEOL metallization system may be attributable to the specific layout of the various circuit elements in those areas, such as closely spaced conductive elements within a given metallization layer, and/or the relative positioning or alignment of circuit elements between successive metallization layers. In still other cases, the anomalies may be related to one or more aspects of the pillar bump, such as the type of material, adhesion, and/or processing issues described above.

In certain cases, the material of a particular pillar bump may be somewhat harder and/or stronger than might normally be expected for a typical pillar bump that is made up of that same type of material. As a result, the overall stiffness of such a pillar bump may be increased relative to that of a typical pillar bump, which, due to its lower hardness and/or material strength, may be somewhat more flexible or compliant when exposed to certain lateral loading schemes. Under such circumstances, the behavioral interaction between a metallization system and a pillar bump that may be made up of a harder and/or stronger material may display a substantially different behavioral interaction curve under a lateral force test relative to that of the typical pillar bumps described above. For descriptive purposes, these pillar bumps that may be made up of a material that is otherwise harder and/or stronger than that of the typical pillar bumps described above may hereinafter be referred to as "stiff" pillar bumps, whereas typical pillar bumps may also be referred to as "compliant" pillar bumps.

In some cases, such anomalous stiff pillar bumps may be formed during the pillar bump process such that the pillar bump includes one or more metal grains which have an otherwise anomalous or imperfect crystalline grain structure. For example, in those illustrative embodiments wherein the pillar bumps of a semiconductor chip are made up of copper or a copper alloy, the elastic and plastic behavior of the copper pillar bumps may depend on the actual texture of the bumps. As noted above, in some cases, this texture could cause some of the copper pillar bumps to be stiffer than a more typical compliant pillar bump with respect to certain loading schemes that are applied to the bumps during lateral load tests—i.e., resulting in a stiff pillar bump, as previously described. Such anomalous stiff pillar bumps may generally be less likely to deflect and/or deform under a given load than would a more typical compliant pillar bump, whether that given load is an out-of-plane thermal interaction load during a flip-chip bonding and assembly process, or a lateral load imposed on the pillar bump during a slow speed lateral load test. Accordingly, since stiff pillar bumps may be less likely to deform under a lateral load, they may also be more likely to be associated with crack-induced failures of a chip's metallization system, since a greater amount of the load on the stiff pillar bump is driven into the weaker underlying metallization layers.

Figure 5:
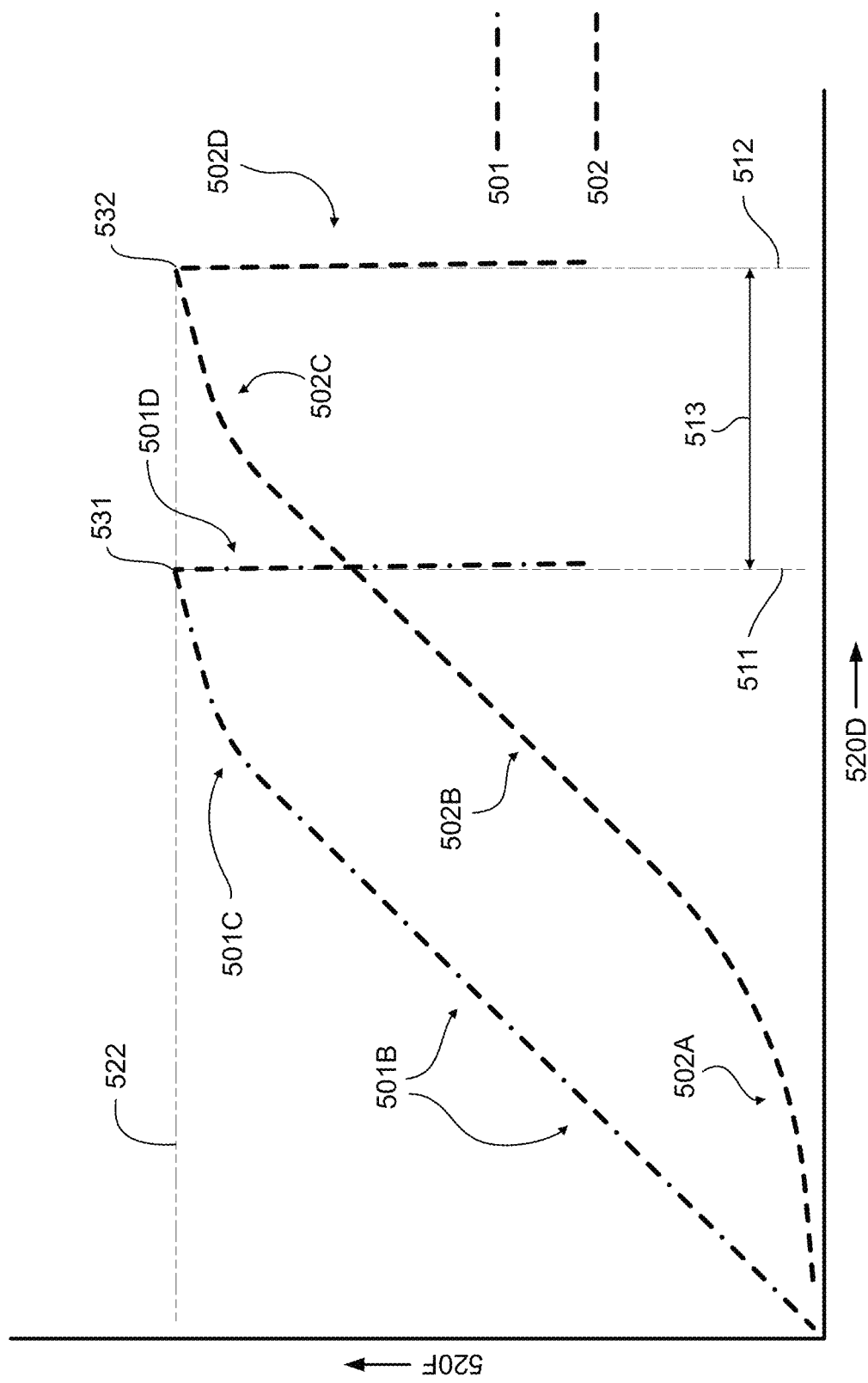
FIG. 5 graphically illustrates comparative curves representing the behavioral interaction between anomalous stiff or typical compliant pillar bumps, and an underlying metallization system of a semiconductor chip or wafer when tested to crack failure using slow-speed lateral force tests and the illustrative test configuration of FIG. 2 disclosed herein.

FIG. 5 graphically illustrates comparative pillar bump/metallization system interaction curves 501 and 502, which represent the behavioral interaction of anomalous stiff pillar bumps and typical compliant pillar bumps, respectively, when tested to crack failure using the illustrative test configuration of FIG. 2. As shown in FIG. 5, curve 502, which represents the typical behavioral interaction between compliant pillar bumps and an underlying metallization system, has a configuration that is substantially the same as the typical force/distance curve 302 illustrated in FIG. 3. More specifically, the compliant pillar bump curve 502 displays an initial non-linear strain-hardening region 502A (correlating to region 302A), a second substantially linear region 502B (correlating to region 302B), a third non-linear region 502C (correlating to region 302C), a crack point 532 (correlating to crack point 332), and a substantially linear post-crack region 502D (correlating to region 302D). Furthermore, it should be understood that the crack point 532 occurs at a force level 522 having substantially the same magnitude as the force level 322 of curve 302, and at a total distance traveled 512 having substantially the same magnitude as the distance 312 of curve 302.

Curve 501, which represents the typical behavioral interaction between stiff pillar bumps and an underlying metallization system, has a configuration that is similar to some aspects of the force/distance curve 502, but different, however, than some other aspects of curve 502. For example, the stiff pillar bump curve 501 has a substantially linear region 501B which has substantially the same slope as the second substantially linear region 502B of curve 502, and a region 501C having substantially the same non-linear configuration as the third non-linear region 502C of curve 502. Furthermore, curve 501 displays a crack point 531 this is at a force level that is substantially the same as the force level 522 of curve 502, as well has a substantially linear post-crack region 501D which has substantially the same slope as the post-crack region 502D of curve 502.

On the other hand, the stiff pillar bump curve 501 does not display a substantially non-linear initial curve region that would be comparable to the non-linear region 502A of the compliant pillar bump curve 502. This may be indicative that the initial strain-hardening effect shown in region 502A (and region 302A of FIG. 3) that influences the force/distance response of compliant pillar bumps does not generally occur with the stiff pillar bumps. Accordingly, since there is no non-linear strain-hardening effects occurring during the initial part of the lateral force tests represented by curve 501, a stiff pillar bump/metallization system may reach its maximum load carrying level 522 more quickly than does a similarly configured compliant pillar bump/metallization system. More specifically, as shown in FIG. 5, curve 501 shows that a crack is created in the stiff pillar bump system at a maximum distance traveled 511 that is less than the distance 512 that is required to initiate a crack in the compliant pillar bump system by an amount 513, as shown by curve 502. Therefore, the data represented by the stiff pillar bump curve 501 indicates that as a given chip package cools and shrinks after the chip reflow process, white bump crack failures will be more likely to occur in those areas of the metallization system that surround or are near anomalous stiff pillar bumps.

In certain illustrative embodiments, the slow speed lateral force tests disclosed herein may be performed on specific semiconductor chips prior to flip-chip packaging so as to detect the presence of anomalous stiff pillar bumps, which, as described above, may be more likely than typical compliant pillar bumps to lead to the occurrence of white bump crack failures in an underlying metallization system. However, in accordance with the present disclosure, adjustments may be made to the slow speed lateral force testing methodology so that the pillar bumps in general are not tested to failure, i.e., so that the presence of stiff pillar bumps is merely detected, but without creating a crack in the underlying metallization system during the test.

Figure 6A:
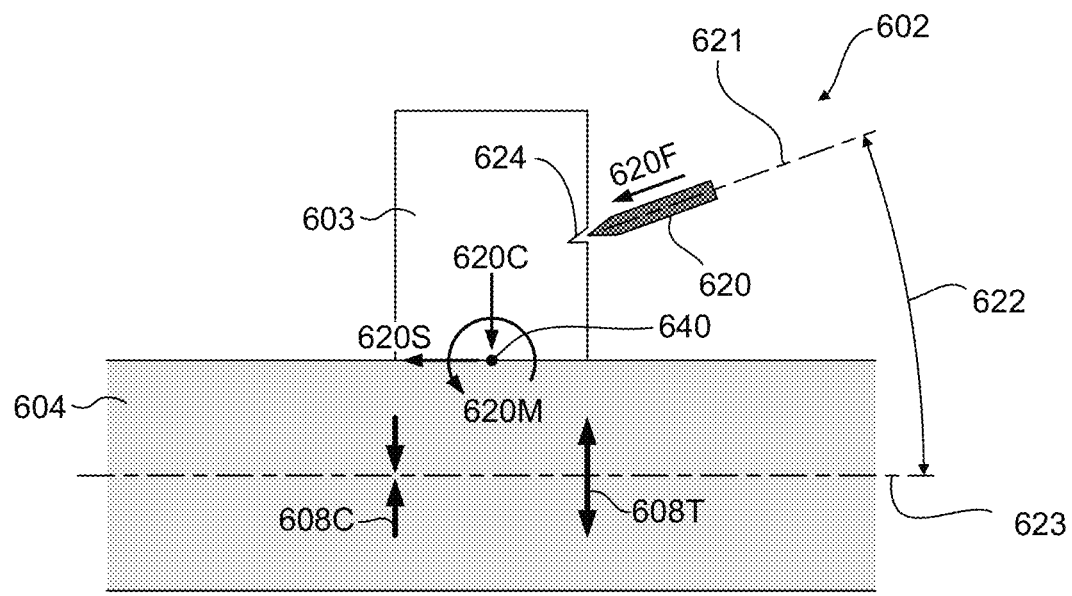
FIGS. 6a and 6b schematically depict test configurations according to some illustrative embodiments disclosed herein that may be used for testing and locating anomalous stiff pillar bumps formed above a metallization system of a semiconductor chip or wafer.

FIG. 6a schematically depicts one illustrative embodiment of the present disclosure wherein a slow speed lateral force test may be used to detect the presence of anomalous stiff pillar bumps formed above a metallization system 604 of a semiconductor chip or wafer 602. As shown in FIG. 6a, a test probe 620 may be used to impose a force 620F on a pillar bump 603, which may represent one of a plurality of pillar bumps 603 of the semiconductor chip 602. In certain embodiments, the test probe 620 may be moved along a path 621 at a constant speed in accordance with the previously described slow speed testing methodology—i.e., at a test probe speed that is less than approximately 0.1 μm/sec—so as to generate the force 620F on the respective pillar bump 603. Furthermore, in order to avoid inadvertently inducing a crack in the metallization system 604 underlying the pillar bump 603 during the slow speed lateral force test shown in FIG. 6a, the probe 620 may be moved along a path that is not substantially parallel to the plane 623 of the metallization system 604, as may have been used to generate the typical behavioral interaction curves 301 and 302 shown in FIG. 3, as well as the curves 501 and 502 shown in FIG. 5. Instead, and for the reasons outlined below, the path 621 along which the test probe 620 may be moved during the test may be angled downward toward the pillar bump 603 and the metallization system 604 at a substantially non-zero angle 622 relative to the plane 623.

It should be appreciated that when the force 620F is imposed on the pillar bump 603 with the probe 620 at the substantially non-zero angle 622, only a first portion of the force vector 620F translates to a shear load 620S and an overturning moment 620M at the interface 640 between the pillar bump 603 and the metallization system 604. On the other hand, a second portion of the force vector 620F imposed on the pillar bump 603 translates to a compressive load 620C at the interface 640. Accordingly, with the overturning moment 620M being reduced from what would typically be the case when the lateral force is imposed along a substantially parallel path relative to the metallization system (see, e.g., the path 212 of the force 220F relative to the plane 223 in FIG. 2), together with the additional compressive load portion 620C, the localized tensile stress 608T in the metallization system 604 may, at least during an initial part of the lateral force test, remain below a stress level that might induce a crack.

In certain embodiments of the present disclosure, the force/distance behavioral interaction of the pillar bump 603 and the metallization system 604 may be evaluated and/or plotted during the lateral force test. Furthermore, in at least some illustrative embodiments, the specific behavioral interaction of a given tested pillar bump 603 may be compared on a real-time basis to the known behavioral interaction curves for anomalous stiff pillar bumps and typical compliant pillar bumps, e.g., the behavioral interaction of pre-characterized typical populations, such as may be represented by the comparative behavioral interaction curves 501 and 502 shown in FIG. 5. Moreover, since stiff pillar bumps have been shown to display a substantially linear response from the very beginning of a lateral force test (see, e.g., region 501B of curve 501), as compared to the substantially non-linear initial response of compliant pillar bumps (see, e.g., region 502A of curve 502), it is possible to quickly assess whether or not a given pillar bump 603 may be an anomalous stiff pillar bump. In some embodiments, slow speed lateral force testing of the pillar bump/metallization system may then continue at least until a statistically significant and/or predetermined quantity of pillar bumps 603 have been tested, at least in the critical areas of the semiconductor chip 602.

In at least some embodiments, the modified slow speed lateral force testing of pillar bumps 603 that is used to detect stiff pillar bumps as described above may be performed with the semiconductor chip 602 mounted on a test fixture (not shown) such that the plane 623 of the metallization system 604 is in a substantially horizontal orientation, as is shown in FIG. 6a, and wherein the test probe 620 is moved along the path 621 at a downwardly oriented angle 622 relative to the horizontal plane. In certain embodiments, the angle 622 may range between about 5° and 45°, wherein the specific angle 622 used may depend on the level of overturning moment 620M to which the metallization system 604 can be safely exposed without inducing a crack. Furthermore, it should be appreciated that, due to the angle 622 of the path 621 along which the test probe 620 is moved during the modified lateral force tests, the notch 624 created in the tested pillar bump 603 may have a substantially asymmetric configuration or appearance, thereby readily distinguishing the angled pillar bump tests that may be used to detect stiff pillar bumps.

Figure 6B:
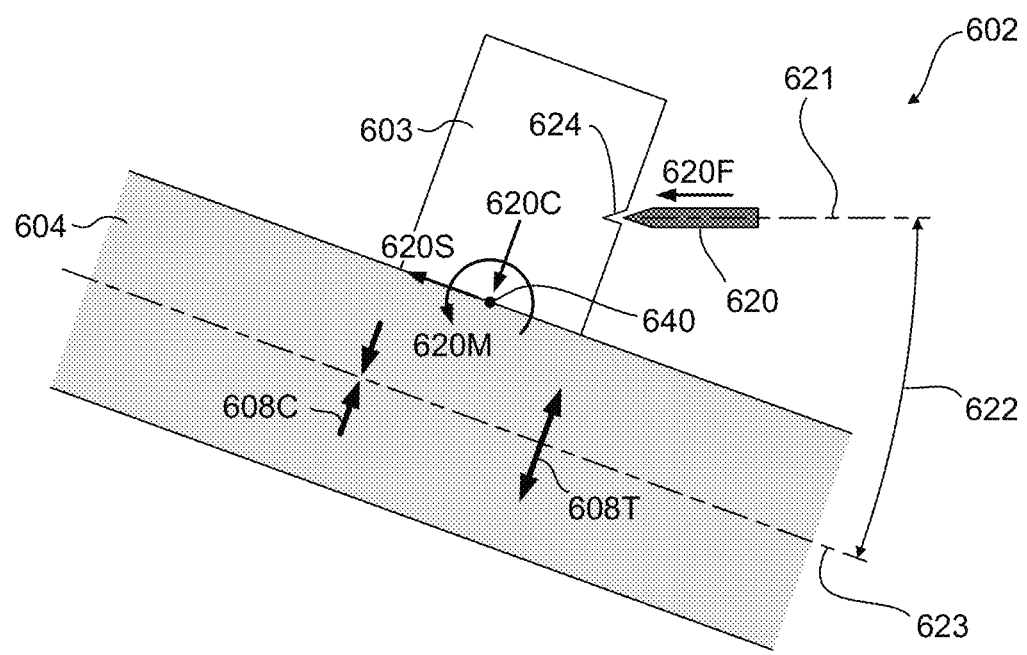

In other embodiments, the semiconductor chip 602 may be mounted on a test fixture (not shown) as described above, wherein however the test fixture and chip 602 may be rotated such that the plane 623 of the metallization system 604 is at an angle 622 relative to horizontal, as is shown in FIG. 6b. During the lateral force tests, the test probe 620 may then be moved along a path 621 that is substantially aligned with the horizontal plane, thereby inducing the same relative magnitudes of loads 620S, 620C and overturning moment 620M at the interface 640 as is described with respect to FIG. 6a above. Accordingly, the same reduced relative level of local tensile stress 608T may be induced in the metallization system 604 during the angled lateral force tests illustrated in FIG. 6b, thus substantially avoiding the creation of cracks.

In some embodiments disclosed herein, when the modified lateral force testing method illustrated in FIGS. 6a and 6b is used to detect anomalous stiff pillar bumps without inducing crack failures in the underlying metallization system of a semiconductor chip, it may be possible to take at least some remedial steps to salvage a chip that contains stiff pillar bumps without having to resort to completely scrapping the chip. Such an approach may be of particular importance in those cases where the semiconductor chip in question may have a relatively greater cost than normal, and/or may be intended for use in more robust, critical, specialized, and/or high end applications. For example, as noted above, a stiff pillar bump may be more likely to lead to crack failures in the underlying metallization system than would a typical compliant pillar bump, due at least in part to the shorter total amount of pillar bump displacement that may be required to induce a load of sufficient magnitude to induce a crack. See, i.e., the comparative behavioral interaction curves 501 and 502 of FIG. 5, showing that a displacement distance 511 (curve 501) is generally required to induce a crack in the metallization system below a typical stiff pillar bump, whereas a greater distance 512 (curve 502) is generally required to induce a crack below a typical compliant pillar bump. Accordingly, an analysis may be performed to evaluate the specific locations on the semiconductor chip where stiff pillar bumps may be located, and a determination made as to whether or not those specific locations may be expected to undergo an amount of differential thermal expansion during chip packaging interaction that would be sufficiently likely to cause crack failures in the underlying metallization system.

On one hand, if any stiff pillar bumps are positioned at specific points on the chip where subsequent white bump failures may be less likely to occur, a risk assessment may be performed to determine whether or not it may be feasible to use the chip as-is. On the other hand, if one or more stiff pillar bumps are located in those regions of the chip where white bump failures are more likely to occur, such as at or near the corners of the chip, additional analysis and/or remedial action may be warranted, as will be further described below.

In those cases where stiff pillar bumps may be located in the regions of a semiconductor chip where white bump defects are more likely to occur, an analysis of the chip's circuit layout below and surrounding the specific points where stiff pillar bumps are positioned may be performed to determine whether those areas of the chip contain sensitive circuit elements that may be adversely affected should a white bump crack occur in the surrounding metallization layers. If not, a further risk assessment may be performed to determine the feasibility of using the chip as-is. However, even if sensitive circuit elements may be present in the areas of the chip below a stiff pillar bump, it may still be possible to use the chip in a less demanding application that may not require an overly robust chip design. Additionally, in at least some illustrative embodiments of the present disclosure, some stiff pillar bumps may be repaired by modifying the flexibility of the pillar bumps as described with respect to FIGS. 7a-7e below, so that the chip might still be used as originally intended, or at least in an application requiring less stringent adherence to the original circuit design layout requirements.

Once a stiff pillar bump has been detected above the metallization system of a semiconductor chip, the stiff pillar bump may be repaired by increasing the pillar bump's flexibility, so that at least some of the out-of-plane loads imposed on the repaired pillar bump during chip packaging thermal interaction may be absorbed by deformation of the bump. This in turn may reduce the magnitude of the loads that are transmitted through the pillar bump's bonding pad (see, e.g., FIG. 1d) and the corresponding level of local tensile stresses that are induced in the underlying metallization system. Accordingly, the likelihood that a crack may occur in one or more of the metallization layers during flip-chip packaging may be thereby reduced.

Figure 7A:
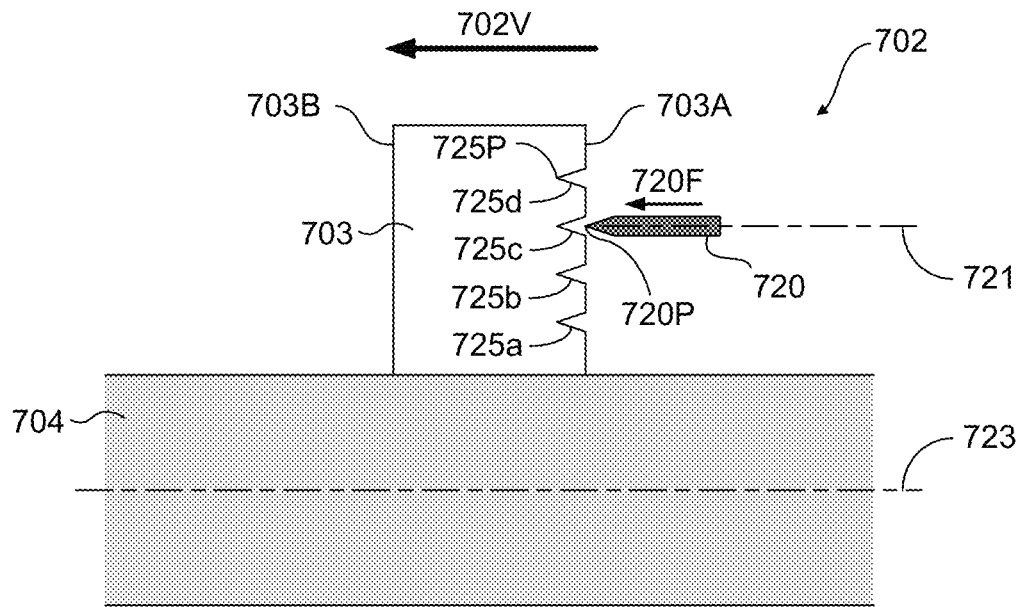

FIG. 7a schematically depicts one embodiment of an illustrative method that may be used for repairing stiff pillar bumps according the present disclosure. As shown in FIG. 7a, a pillar bump repair device 720 may be used to form a plurality of strain-relieving notches along one side 703A of a respective stiff pillar bump 703, such as the notches 725a-d, which may provide a degree of spring-like flexibility to the stiff pillar bump 703. The strain-relieving notches 725a-d may be formed by contacting the stiff pillar bump 703 with the tip 720P of the pillar bump repair device 720, thereby imposing a force 720F that is sufficiently high enough to locally deform the bump 703 at the location of each notch 725a-d. In some illustrative embodiments, the pillar bump repair device 720 may be moved along a path 721 that is substantially parallel to the plane 723 of the metallization system 704, although it should be appreciated that a non-parallel path may also be used, depending on the degree of additional pillar bump flexibility required.

In certain disclosed embodiments, the path 721 of the pillar bump repair device 720 may be substantially aligned with a radial vector 702V that points toward the approximate center 702C of the semiconductor chip 702 (see, FIG. 7c), so that the stress-relieving notches 725a-d may be oriented along the path of the greatest out-of-plane loads imposed on the chip 702 during flip-chip packaging. See, e.g., the force vectors 102F illustrated in FIG. 1c and described above. The stress-relieving notches 725a-d that are formed in accordance with the steps outlined above may therefore be positioned along the side 703A of the stiff pillar bump that is oriented substantially away from the approximate center 702C of the semiconductor chip 702, and substantially toward the periphery of the chip 702 (not shown in FIG. 7a), which corresponds to the tensile load side of the pillar bump 703. See, e.g., the local tensile stress 208T shown in FIG. 2. Moreover, in at least some embodiments, the notches 725a-d may be positioned along the side 703A in a substantially vertical alignment. Accordingly, the notches 725a-d may hereinafter be referred to as tensile strain-relieving notches, as they may tend to provide additional bump flexibility on the tensile load side of the pillar bump 703.

The actual quantity of tensile strain-relieving notches formed along the side 703A of the stiff pillar bump 703, as well as the depth of each respective notch, may depend on the degree of additional flexibility that may be required for the repaired pillar bump in question. For example, stiff pillar bumps that are positioned in areas of a semiconductor chip where a greater amount of differential thermal expansion occurs, such as locations that are the farthest distance from the center of the chip (see, e.g., the corner regions 102E of the chip 102 shown in FIG. 1c) may require a greater degree of additional pillar bump flexibility, and therefore may have more and/or deeper strain-relieving notches. Similarly, stiff pillar bumps that may be positioned above or near areas of the metallization system containing sensitive or critical circuit elements may also require greater added flexibility so as to reduce the likelihood that cracks may occur in those areas, thus necessitating more and/or deeper notches.

Figure 7B:
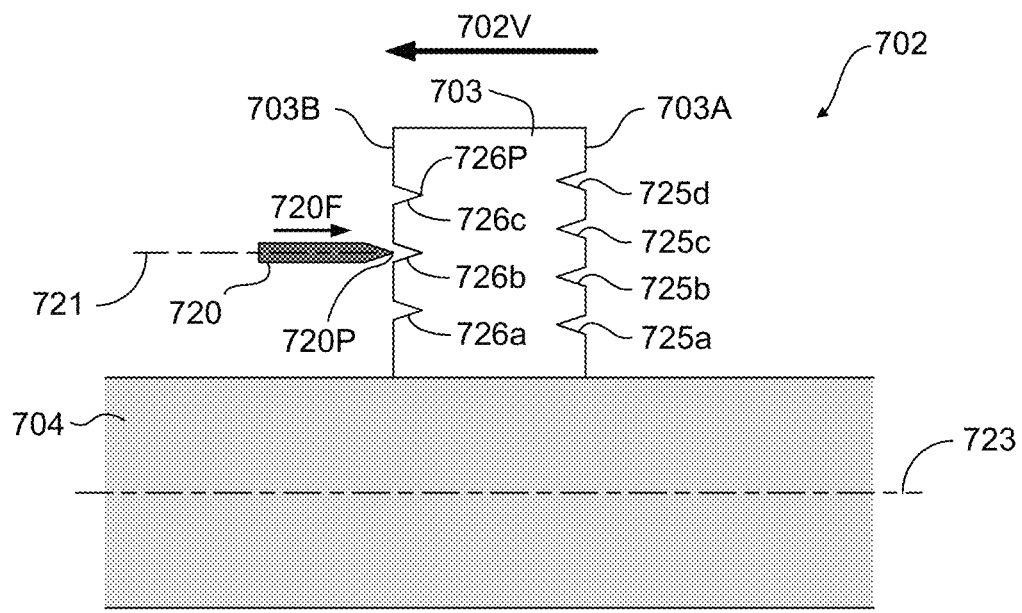

FIG. 7b schematically illustrates another exemplary method for increasing the flexibility of the stiff pillar bump 703 depicted in FIG. 7a, wherein additional strain-relieving notches, such as the notches 726a-c, may be formed on an opposite side 703B of the stiff pillar bump 703 from the first side 703A where the initial strain-relieving notches 725a-d may have been formed, as described above. As shown in FIG. 7b, the notches 726a-c may be formed by moving the pillar bump repair device 720 substantially along the same path 721 as described with respect to FIG. 7a above so as to impart a force 720F that locally deforms the stiff pillar bump 703 at the location of each additional notch 726a-c. However, as shown in FIG. 7b, the pillar bump repair device 720 is moved in an opposite direction relative to the stiff pillar bump 703 so that the tip 720P contacts the stiff pillar bump 703 on an opposite side 703B from the side 703A. Therefore, in at least some embodiments, the stress-relieving notches 726*a-c* may be oriented substantially toward the approximate center 702C of the semiconductor chip 702 (see, FIG. 7*c*), and away from the periphery of the chip 702 (not shown), which corresponds to the compressive load side of the pillar bump 703. See, e.g., the local compressive stress 208C shown in FIG. 2. Moreover, as with the notches 725*a-d* above, in certain illustrative embodiments, the notches 726*a-c* may also be positioned along the side 703B of the stiff pillar bump 703 in a substantially vertical alignment. Accordingly, the notches 726*a-c* may hereinafter be referred to as compressive strain-relieving notches, as they may tend to provide additional bump flexibility on the compressive load side of the pillar bump 703. Furthermore, and as noted above, the actual quantity and depth of the compressive strain-relieving notches formed on the side 703B oriented toward the approximate center 702C of the semiconductor chip 702, such as the notches 726*a-c*, may be adjusted as required for the desired final flexibility of the stiff pillar bump 703 after the above described repair modifications have been performed.

In some illustrative embodiments, the position of one or more of the above described strain-relieving notches and the depth to which the notches are formed may be limited by one or more of the specific design parameters associated with a given pillar bump. For example, the presence of the strain-relieving notches described herein may reduce, to at least some degree, the cross-sectional area of a repaired pillar bump. As such, in certain embodiments the notch depths may be limited so as to avoid increasing the current density in a repaired pillar bump, thereby avoid, or at least minimize, any electromigration effects that may result from the reduced cross-sectional area. Similarly, the proximity of a given strain-relieving notch to the top or bottom end of the repaired pillar bump may also be limited for the same reasons, as the current density in the pillar bump may be highest in those areas.

FIG. 7*c* schematically depicts a plan view of the stiff pillar bump 703 shown in FIGS. 7*a* and 7*b*, illustrating further illustrative embodiments of the stiff pillar bump repair methods disclosed herein. In certain embodiments, a pillar bump support device 730, such as a collar-shaped support device and the like, may be used to substantially prevent the force 720F used to form each strain-relieving notch in the stiff pillar bump 703 from causing the type of pillar bump displacement that commonly occurs during the lateral force testing of pillar bumps. See, e.g., the force/distance curves 301 and 302 of FIG. 3, and the force/distance curves 501 and 502 of FIG. 5.

In operation, the pillar bump support device 730 may be positioned adjacent to a stiff pillar bump 703 so that a contact surface 730S of the pillar bump support device 730 is substantially in contact with at least a portion of the stiff pillar bump 703. In certain embodiments, the pillar bump support device 730 may be held in place during the pillar bump repair process by an appropriate tool (not shown) on the opposite side of the stiff pillar bump 703 from where the strain-relieving notches are being formed with the pillar bump repair device 720. For example, when the tensile strain-relieving notches 725*a-d* are being formed along the side 703A of the stiff pillar bump 703 that is oriented away from the approximate center 702C of the semiconductor chip 702, the pillar bump support device 730 may be positioned on the opposite side 703B of the pillar bump 703, as shown in FIG. 7*c*. Similarly, when the compressive strain-relieving notches 726*a-c* are being formed along the side 703B of the stiff pillar bump 703 that is oriented toward the center approximate 702C, the pillar bump support device 730 may be positioned on the opposite side 703A. In this way, the notch-creating force 720F will generally not be transmitted into the underlying metallization system 704 (see, e.g., FIGS. 2, 6*a*. and 6*b*), but will instead be resisted by a reaction force 730F that is imposed on the stiff pillar bump 703 by the pillar bump support device 730. Accordingly, the repair system shown in FIG. 7*c* will substantially be in force equilibrium during the above-described pillar bump repair process, and the possibility that cracks may be created in the metallization system 704 by the force 720F may be substantially avoided.

In some embodiments, at least a portion of the pillar bump support device 730 may have a shape that substantially conforms to the shape of the stiff pillar bump 703, so that it may thereby provide adequate support during the pillar bump repair processes described herein. For example, when the stiff pillar bump 703 has a substantially cylindrical shape as shown in FIG. 7*c*, the portion of the pillar bump support device 730 that is adapted to contact the pillar bump 703 may have a substantially similar cylindrical shape. In such embodiments, the pillar bump support device 730 may be, for example, a portion of a hollow cylinder, such as half of a hollow cylinder, as shown in FIG. 7*c*. However, it should be appreciated that the half hollow cylinder configuration shown in FIG. 7*c* is illustrative only, as other configurations or shapes may also be used, so long as they provide the requisite degree of support, as described above. Furthermore, the pillar bump support device 730 may also be made up of any suitable material that may be capable of providing an appropriate degree of support, and substantially without creating any additional surface damage to the repaired pillar bump 703. By way of example only, the pillar bump support device 730 may be made of a resilient gasket-like material, such as rubber and the like, although it should be understood that other materials, both harder and softer, may also be used within the spirit and scope of the present disclosure.

In certain embodiments, the pillar bump repair device 720 used to form the stress-relieving notches 725*a-d* and/or 726*a-c* may be, for example, a test probe, such as the test probes 220 or 620 described herein that may typically be used for performing lateral force tests. In other embodiments, the pillar bump repair device 720 may be a specialized tool such that the tip 720P has a specific tip contour, as will be further described with respect to FIGS. 7*d* and 7*e* below.

During the above-described pillar bump repair process, the material of the pillar bump surrounding the inside tip of any given strain-relieving notch, such as the inside tips 725P and/or 726P shown in FIGS. 7*a* and 7*b*, may become strain hardened as a respective notch indention is formed. Furthermore, as the shape of the tip 720P on the pillar bump repair device 720 approaches a sharper point, the amount of strain hardening induced during the notch deformation process may increase. As noted above, the test probe that is used to perform lateral force tests for detecting stiff pillar bumps (such as the test probe 620 shown in FIGS. 6*a* and 6*b*) may sometimes also be used to form the strain-relieving notches during the pillar bump repair process. However, in those illustrative embodiments wherein the test probe used to detect stiff pillar bumps may have a substantially pointed tip 720P, a pillar bump repair device having a tip 720P that does not induce such a great degree of strain hardening during notch formation may instead be used during the pillar bump repair process, as described below.

FIG. 7*d* is a close-up view of the tensile strain-relieving notches 725*a-d* formed in the stiff pillar bump 703 of FIGS. 7*a* and 7*b*. As shown in FIG. 7*d*, the tip 720P of the pillar bump repair device 720 may have a radiused contour 720R, which may then be used to form one or more of the notches 725a-d with an inside notch tip 725P having a radiused contour 725R that is substantially the same as the radius 720R. The radius-tipped notches 725a-d may therefore cause a lower overall degree of strain hardening in the surrounding material of the stiff pillar bump 703, thereby increasing to some degree the amount of flexibility that is added to the pillar bump 703 by virtue of the above-described pillar bump repair process. Furthermore, it should be understood that when strain-relieving notches are also formed on an opposite of the stiff pillar bump 703, such as the compressive strain-relieving notches 726a-c shown in FIGS. 7b and 7c, the pillar bump repair device 720 having a tip 720P with a radiused contour 720R may also be used so as to reduce the degree of material strain hardening that may be caused in those locations during notch formation.

In other illustrative embodiments disclosed herein, the pillar bump repair device 720 having a tip 720P with a radiused contour 720R may also be used to reduce the degree of strain hardening that may have been induced in the area surrounding any notch that may have been formed using a test probe having a substantially sharp-pointed tip. For example, as shown in FIG. 7e, the radiused-tipped pillar bump repair device 720 shown in FIG. 7d may be used to adjust the profile a previously formed notch 724 having a substantially sharp-pointed inside notch tip 724T, so that the adjusted profile of the notch 727 may have an inside notch tip 727P with a radiused contour 727R that substantially matches the radiused contour 720R of the tip 720P on the pillar bump repair device 720. Furthermore, in at least some embodiments, the profile of any notches formed in a given pillar bump when lateral force testing is being used to detect the presence of stiff pillar bumps, such as the notches 624 in the pillar bumps 603 shown in FIGS. 6a and 6b, may adjusted in a similar fashion by using a radius-tipped pillar bump repair device, such as the device 720 having a tip 720P with a radiused contour 720R.

Figure 8:
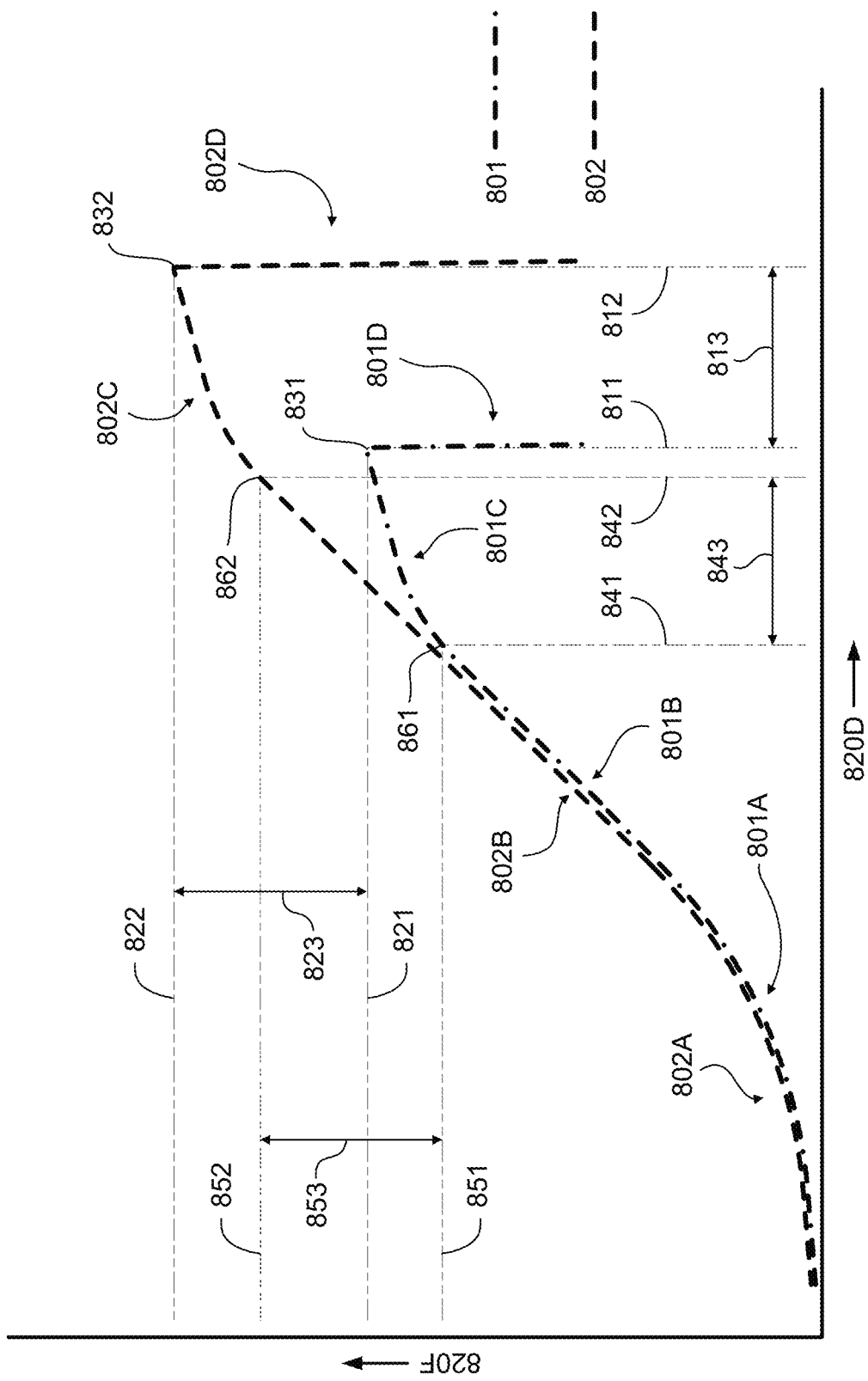
FIG. 8 graphically depicts the comparative difference between a curve that represents the typical behavioral interaction of pillar bumps that are formed above a metallization system of a semiconductor chip or wafer, and a curve that represents the behavioral interaction of pillar bumps that are formed above anomalous weak sites in a metallization system when tested to crack failure using slow-speed lateral force tests and the illustrative test configuration of FIG. 2 disclosed herein.

FIG. 8 graphically illustrates comparative pillar bump/metallization system behavioral interaction curves 801 and 802, wherein curve 801 depicts a behavioral interaction curve of pillar bumps that have been formed above anomalous weak sites in the BEOL metallization system of a semiconductor chip or wafer, whereas curve 802 depicts a typical comparative behavioral interaction curve of a representative pillar bump/metallization system configuration. As shown in FIG. 8, comparative behavioral interaction curve 802 has a configuration that is substantially the same as the typical comparative force/distance behavioral interaction curves 302 and 502 illustrated in FIGS. 3 and 5, respectively. More specifically, curve 802 displays an initial non-linear, e.g., strain-hardening, region 802A (correlating to regions 302A/502A), a second substantially linear region 802B (correlating to regions 302B/502B), a third non-linear region 802C (correlating to regions 302C/502C), a crack point 832 (correlating to crack points 332/532), and a substantially linear post-crack region 802D (correlating to regions 302D/502D). Furthermore, it should be understood that the crack point 832 occurs at a force level 822 having substantially the same magnitude as the force levels 322/522 of curves 302/502, and at a total distance traveled 812 having substantially the same magnitude as the distances 312/512 of curves 302/502.

Curve 801, which, as noted above, depicts the representative behavioral interaction of pillar bumps that have been formed above anomalous weak sites of a BEOL metallization system, has a configuration that is similar to some aspects of the typical force/distance curve 802, but different, however, than some other aspects of curve 802. For example, as shown in FIG. 8, curve 801 has a substantially non-linear initial 801A that closely follows the shape of the initial non-linear region 802A of the typical comparative force/distance behavioral interaction curve 802. Additionally, curve 801 has a linear region 801B which has substantially the same slope as the second substantially linear region 802B of curve 802, and furthermore closely follows curve 802 up to an approximate transition point 861, which is indicative of a lateral force 820F on a representative pillar bump having a magnitude 851 and a distance traveled 820D having a magnitude 841.

However, after having reached the end of the substantially linear response region 801B at the approximate transition point 861, curve 801 transitions into a substantially non-linear response region 801C, which has a substantially similar non-linear configuration as the third non-linear region 802C of curve 802, albeit occurring in a lower range of force 820F and a shorter range of distance traveled 820D. For example, as shown in FIG. 8, the comparative behavioral interaction curve 802 displays an approximate linear to non-linear transition point 862 between regions 802B and 802C that occurs at a lateral force magnitude 852, which is greater by an amount 853 than the lateral force magnitude 851 for the transition point 861 of curve 801. In one example, the force 852 may be approximately 10-50% greater than the force 851. Furthermore, the transition point 862 also occurs at a distance traveled 842 that is greater than the distance traveled 841 shown for curve 801 at the transition point 861 by an amount 843. In one example, the distance 842 may be approximately 5-35% greater than the distance 841.

Curve 801 further indicates that a crack will eventually occur at anomalous weak BEOL sites at a force level 820F and distance traveled 820D that are both lower than the respective values indicated for the typical pillar bump/metallization system configuration depicted by curve 802. More specifically, curve 801 displays a crack point 831 that occurs at a force level 820F having a magnitude 821 that is lower by an amount 823 than the magnitude 822 of the force level 820F that is required to initiate a crack in the typical pillar bump/metallization system configuration as indicated by crack point 832. Similarly, accordingly to curve 801, the total distance traveled 820D to initiate a crack in the weak BEOL metallization system during lateral force tests has a magnitude 811, which is less than the corresponding magnitude 812 of curve 802 by an amount 813.

Accordingly, a comparison of the force/distance response curves 801 and 802 provides evidence that a system configuration that is made up of typical pillar bump (e.g., a compliant pillar bump as previously described) will generally display, at least up to a point, a common force/distance behavioral interaction response, irrespective of whether or not the pillar bump is located near or above an anomalous weak BEOL metallization system site. However, when the tested pillar bump is positioned above or near an aforementioned anomalously weak BEOL site, the behavioral interaction curve of the tested pillar bump will transition from a substantially linear response to a substantially non-linear at a lower lateral force level and distance traveled than would normally be expected for a typical pillar bump/metallization system configuration. This type of pillar bump/metallization system behavioral interaction may therefore be used in some instances to perform additional lateral force tests on representative semiconductor chips or wafers so as to detect the presence of anomalous weak BEOL sites in a given metallization system.

In certain illustrative embodiments, slow speed lateral force tests as disclosed herein may be performed on the pillar bumps of specific semiconductor chips prior to flip-chip packaging so as to detect the presence of anomalous weak BEOL sites in an underlying metallization system, which, as described above, may be more likely to lead to the occurrence of white bump crack failures. However, as with the above-described lateral force tests that may be used to detect the presence of anomalous stiff pillar bumps (see, e.g., FIGS. 6a and 6b and the corresponding description), adjustments may be made to the slow speed lateral force testing scheme so that the pillar bumps are not tested to failure, i.e., so that the presence of weak BEOL sites is merely detected, but without creating a crack in the underlying metallization system during the test.

Figure 9A:
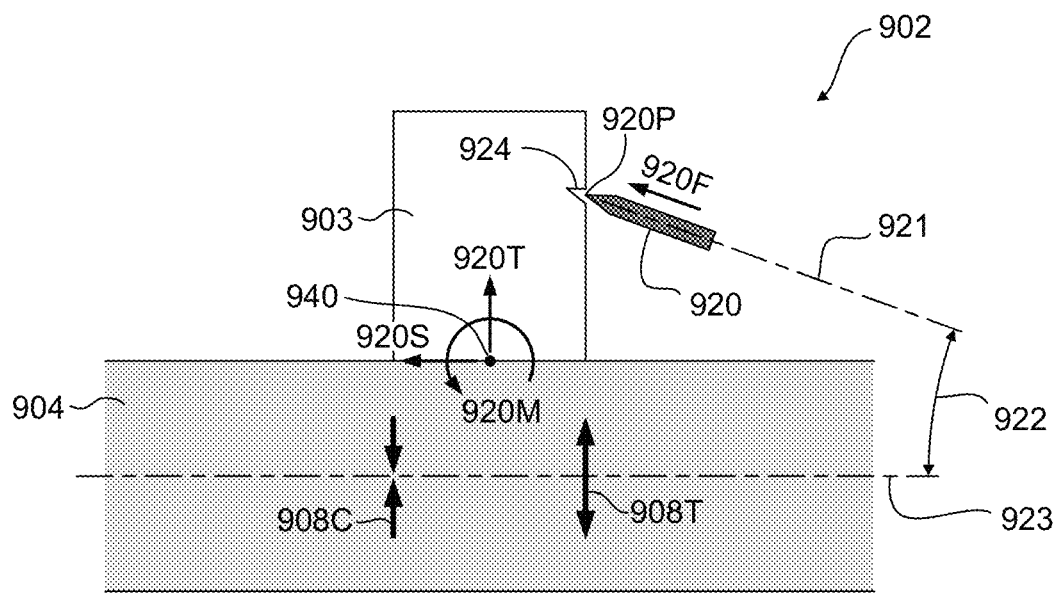
FIGS. 9a and 9b schematically depict test configurations according to some illustrative embodiments disclosed herein that may be used for testing pillar bumps formed above a metallization system of a semiconductor chip or wafer so as to locate anomalous weak sites in the underlying metallization system.

FIG. 9a schematically depicts one illustrative embodiment of the present disclosure wherein a slow speed lateral force test may be used to detect the presence of anomalous stiff pillar bumps formed above a metallization system 904 of a semiconductor chip or wafer 902. As shown in FIG. 9a, a test probe 920 may be used to impose a force 920F on a pillar bump 903, which may represent one of a plurality of pillar bumps 903 of the semiconductor chip 902. In certain embodiments, the test probe 920 may be moved along a path 921 at a constant speed in accordance with the previously described slow speed testing methodology—i.e., at a test probe speed that is less than approximately 0.1 µm/sec—so as to generate the force 920F on the respective pillar bump 903. Furthermore, in order to enhance the ability to detect weak BEOL sites in the metallization system 904 underlying the pillar bump 903 during the slow speed lateral force test shown in FIG. 9a, the probe 920 may not be moved along a path that is substantially parallel to the plane 923 of the metallization system 904, as may have been used to generate the typical behavioral interaction curves 301 and 302 shown in FIG. 3, as well as the curves 801 and 802 shown in FIG. 8. Instead, and for the reasons outlined below, the path 921 along which test probe 920 is moved during the test may be angled at a substantially non-zero angle 922 relative to the plane 923 so that the tip 920P of the test probe 920 contacts the pillar bump 903 at a generally upward tilt.

It should be understood that when the force 920F is imposed on the pillar bump 903 with the probe 920 at the substantially non-zero angle 922, only a first portion of the force vector 920F translates to a shear load 920S and an overturning moment 920M at the interface 940 between the pillar bump 903 and the metallization system 904. On the other hand, a second portion of the force vector 920F imposed on the pillar bump 903 translates to a tensile load 920T at the interface 940. In this load configuration, the total uplift load on the pillar bump 903 due to the combination of the overturning moment 920M and the additional tensile load portion 920T, the localized tensile stress 908T in the metallization system 904 may be higher than what would typically be expected, compared to the load configuration that would typically occur when the lateral force is imposed along a substantially parallel path relative to the metallization system (see, e.g., the path 212 of the force 220F relative to the plane 223 in FIG. 2). In this way, when the tested pillar bump 903 is positioned above or near an anomalously weak BEOL site in the metallization system 904, the transition point from a substantially linear to a substantially non-linear behavioral response, such as the transition point 861 between the regions 802B and 802C of comparative behavioral interaction curve 802 in FIG. 8, would be expected to occur more quickly than might otherwise be the case, thereby enhancing weak site detection.

In certain embodiments of the present disclosure, the force/distance behavioral interaction of the pillar bump 903 and the metallization system 904 may be evaluated and/or plotted during the lateral force test. Furthermore, in at least some illustrative embodiments, the specific behavioral interaction of a given tested pillar bump 903 may be compared on a real-time basis to the known behavioral interaction curves for pillar bumps formed above anomalous weak BEOL sites and the typical pillar bump/metallization system, e.g., the behavioral interaction of pre-characterized typical populations, such as may be represented by the comparative behavioral interaction curves 801 and 802 shown in FIG. 8. Moreover, since pillar bumps formed above weak BEOL sites have been shown to display a quicker transition from a substantially linear response to a substantially non-linear response during a lateral force test (see, e.g., transition point 861 of curve 801) as compared to the same transition in a typical pillar bump/metallization system configuration (see, e.g., the approximate transition point 862 of curve 802), it is possible to quickly assess whether or not a given pillar bump 903 may be formed above an anomalously weak site within the BEOL metallization system 904.

For example, when the force 920F imposed on the pillar bump 903, or the distance traveled by the test probe 920 during the lateral force tests, passes a level that is known to cause an early linear to non-linear behavioral response transition in tests performed on pillar bumps formed above weak BEOL sites (see, FIG. 8), it may be indicative that the tested pillar bump 903 is not located above or near an anomalous weak BEOL site. On the other hand, an early linear/non-linear transition during the later force test may be indicative of a weak site in the BEOL metallization system 904 below the pillar bump 903. Irrespective of whether or not a weak BEOL site has been detected during the lateral force test described above, once the force 920F or the distance traveled by the test probe 920 has passed the range within which the linear/non-linear transition point is generally known to occur, the test may be discontinued prior to inducing a crack in the underlying metallization system. Furthermore, it should be appreciated that in certain illustrative embodiments, a suitable lateral support device, such as the pillar bump support device 730 shown in FIG. 7c and described above, may be used to reduce the magnitude of the bending load imposed on the pillar bump 903 during the above-described tests, thus reducing the likelihood that cracks may occur.

In at least some embodiments, the modified slow speed lateral force testing of pillar bumps 903 that is used to detect stiff pillar bumps as described above may be performed with the semiconductor chip 902 mounted on a test fixture (not shown) such that the plane 923 of the metallization system 904 is in a substantially horizontal orientation, as is shown in FIG. 9a, and wherein the test probe 920 is moved along the path 921 at an angle 922 that is angled upward relative to the horizontal plane. In certain embodiments, the angle 922 may range between about 5° and 45°, wherein the specific angle 922 used may depend on the degree of weak BEOL site detection enhancement that may be desired for the specific semiconductor chip 902 and metallization system 904 being tested. Furthermore, it should be appreciated that, due to the angle 922 of the path 921 along which the test probe 920 is moved during the modified lateral force tests, the notch 924 created in the tested pillar bump 903 may have a substantially asymmetric configuration or appearance, thereby readily distinguishing the angled pillar bump tests that may be used to detect anomalous weak BEOL sites.

Figure 9B:
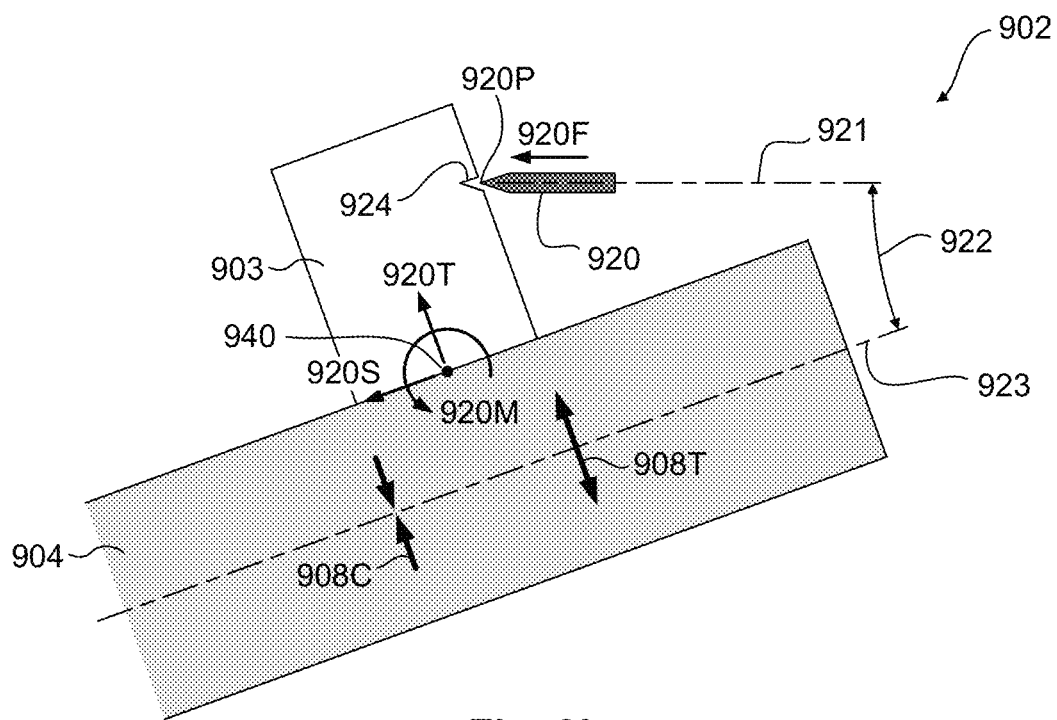

In other embodiments, the semiconductor chip 902 may be mounted on a test fixture (not shown) as previously described, wherein however the test fixture and chip 902 may be rotated such that the plane 923 of the metallization system 904 is at an angle 922 relative to horizontal, as is shown in FIG. 9b. During the lateral force tests, the test probe 920 may then be moved along a path 921 that is substantially aligned with the horizontal plane, thereby inducing the same relative magnitudes of loads 920S, 920T and overturning moment 920M at the interface 940 as is described with respect to FIG. 9*a* above. Accordingly, the same enhanced level of local tensile stress 908T may be induced in the metallization system 904 during the angled lateral force tests illustrated in FIG. 9*b*, thus substantially enhancing the detection of anomalously weak BEOL sites in the metallization system 904.

In some embodiments, slow speed lateral force testing of the pillar bump/metallization system as disclosed herein may then continue at least until a statistically significant and/or predetermined quantity of pillar bumps 903 have been tested, at least in those areas of the semiconductor chip 902 that may be of interest, depending on the specific reasons for performing the tests. For example, in certain illustrative embodiments, the above-described weak BEOL site detection testing may be used to evaluate the robustness of a specific metallization system layout. Depending on the outcome of the weak site detection testing, the specific chip layout may be used for the intended application as-is, the layout may be adjusted as required so as to eliminate and/or design around some or all of the detected weak sites, or the specific layout may be categorized for less robust applications and thereafter used as-is in less critical or less demanding applications.

In certain other embodiments, testing for anomalous weak BEOL sites may be used to evaluate the performance of specific dielectric materials in a given metallization system configuration, or to evaluate the relative performance of new dielectric materials for use in highly scaled new device generations. In still other embodiments, weak site testing may be used as a quality control tool to pre-test dies for flip-chip bonding and assembly readiness, to evaluate process excursions and/or process drift in the back end of line manufacturing stages, or to evaluate the overall health of the manufacturing line (e.g., tool and/or substrate cleanliness, and the like).

Due to the generally upward tilt of the angle 922 at which the test probe 920 contacts the pillar bump 903 relative the plane 923 of the metallization system 904 during the testing for anomalous weak BEOL sites as described above, the tip 920P of the test probe 920 may sometimes move or slide across the outer surface 903S of the pillar bump 903 before the notch 924 begins being formed. Accordingly, in some illustrative embodiments of the present disclosure, the tip 920P of the test probe 920 may be adapted so that it grabs or digs into the surface 903S of the pillar bump 903 rather than sliding across the surface 903S as described above, thereby providing a more consistently repeatable detection test for weak BEOL sites that may be present in the metallization system 904. FIGS. 9*c*-9*l* depicts various illustrative embodiments of test probe tips 920P that may be used for testing pillar bumps 903 in accordance with one or more of the testing configurations illustrated in FIGS. 9*a* and 9*b*, as will be described in further detail below.

Figure 9C:
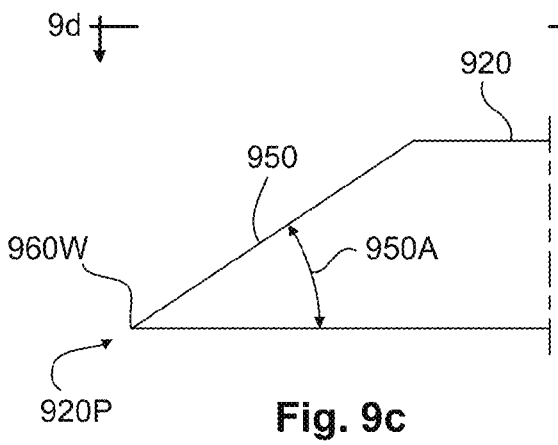
Figure 9D:
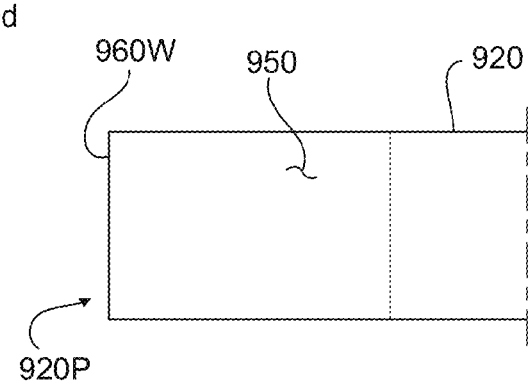

FIG. 9*c* is a side elevation view of one embodiment of a tip 920P of an illustrative test probe 920, and FIG. 9*d* shows the plan view of the test probe 920 in FIG. 9*c* along the view "9*d*-9*d*." As shown in FIGS. 9*c* and 9*d*, the tip 920P of the test probe 920 may have a tapered top surface 950 defining an included angle 950A so that the tip 920P forms a chisel-like wedge shape 960W. In at least some embodiments, the included angle 950A may range on the order of 30-40°, although other angles may also be used. Furthermore, in certain embodiments, the included angle 950A may be adjusted as required so as to provide the requisite degree of tip sharpness, e.g., so that the wedge shape 960W of the tip 920P grabs or digs into the surface 903S of the tested pillar bump 903 (see, FIGS. 9*a* and 9*b*) substantially without moving or slipping. Moreover, the included angle 950A may also be adjusted based on the specific materials of the test probe 920 and the pillar bumps 903 so to minimize the amount of undue deformation or other damage to the wedge shape 960W during repeated pillar bump testing.

Figure 9E:
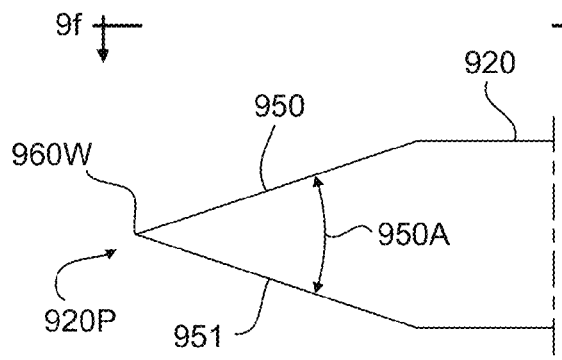
Figure 9F:
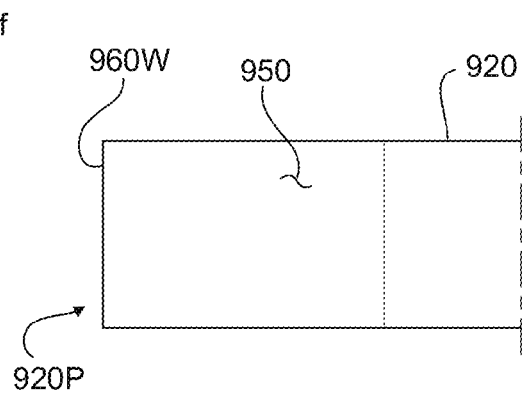

FIGS. 9*e* and 9*f* depict another illustrative embodiment of a test probe 920 having a tip 920P that forms a wedge shape 960W, wherein the tip 920P may also have a tapered bottom surface 951, which together with the tapered top surface 950 forms the included angle 950A. In certain embodiments, the included angle 950A may be approximately 30-40°, although the included angle 950A may be adjusted to other specific angles as may be required so as to provide the requisite degree of tip sharpness, and/or to minimize the amount of undue deformation or other damage to the wedge shape 960W during repeated pillar bump testing, as previously described.

Figure 9G:
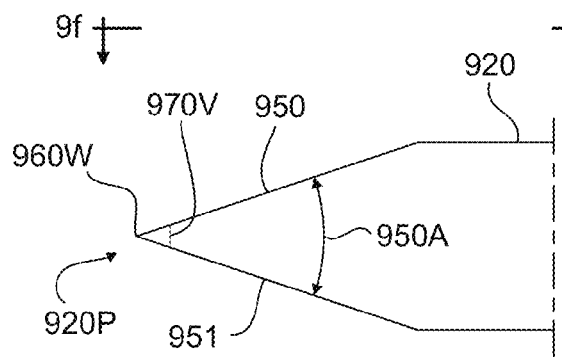
Figure 9H:
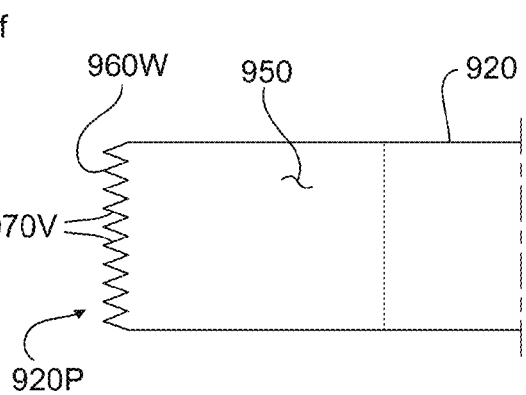

FIGS. 9*g* and 9*h* depict yet another illustrative test probe 920 having a tip 920P that is substantially similar to the tip configuration shown in FIGS. 9*e* and 9*f*—i.e., with tapered top and bottom surfaces 950 and 951 forming a wedge shape 960W, and wherein the tip 920P also includes a plurality of vertically oriented serrations 970V. As shown in the plan view of the test probe 920 illustrated in FIG. 9*f*, the vertically oriented serrations 970V may, in at least some embodiments, extend across the full width of the wedge shape 960W. In other embodiments (not shown), the serrations 970V may be substantially centrally located on the tip 920P with un-serrated portions of the wedge shape 960W near each side, or vice versa, wherein the serrations 970 are grouped near either side of the tip 920P with an un-serrated central portion. Furthermore, as with the included angle 950A of the top and bottom surfaces 950 forming the wedge shape 970W, the size and shape of the vertically oriented serrations 970V may be adjusted as required so as to reduce the likelihood that the tip 920P may slip during its initial contact with the sides 903S of the tested pillar bump 903—e.g., so that the tip 920P may more firmly engage with or grip the pillar bump 903—while also substantially reducing the likelihood of deformation and/or damage to the serrations 970V.

FIGS. 9*i* and 9*j* show yet another illustrative configuration of a test probe 920 having a tip 920P that may be used to substantially reduce the likelihood that the test probe 920 does not slip when the tip 920P initially engages the surface 903S of a respective tested pillar bump 903. In some embodiments, the tip may have top and bottom tapered surfaces 950 having an included angle 950A as previously described with respect to FIGS. 9*c*-9*f* above. However, as shown in the illustrative embodiment depicted in FIGS. 9*i* and 9*j*, the tip 920P may have a substantially truncated or flat surface 960F that includes a plurality of substantially horizontally oriented serrations 970H. Furthermore, in certain embodiments, the tip 920P of test probe 920 may also have tapered side surfaces 952 having an included angle 952A, as shown in FIG. 9*j*. Depending on the parameters associated with the specific weak BEOL site testing, such as pillar bump materials, test probe materials, metallization system configuration, and the like, the included angle 952A may range from approximately 20-40°, although it should be understood that other angles may also be used, as previously described with respect to the included angle 950A described above. It should also be appreciated that any of the previously disclosed embodiments described above, such as the embodiments illustrated in FIGS. 9*c*-9*g*, may similarly have tapered side surfaces 951 as shown in FIG. 9*j*. Also as previously described, the included angles 950A and 952A and the number and size of horizontally oriented serrations 970H may be adjusted as required based on the various pillar bump parameters and testing requirements.

FIGS. 9k and 9l depict a further illustrative embodiment of a test probe 920, wherein the tip 920P of the test probe 920 may have a substantially flat surface 960F. In certain embodiments, the substantially flat surface 960F may be serrated in both the vertical and horizontal directions, such that the tip 920P is made up of a plurality of teeth 970T having a substantially pyramidal shape, and which may be adapted to grab or dig into the surface 903S of a tested pillar bump 903 (see, FIGS. 9a and 9b), rather than slide across the surface 903S as described above. Furthermore, it should also be appreciated that the double-serrated/pyramidal teeth configuration illustrated in FIGS. 9k and 9l may also be used, for example, on the truncated or flat surface 960F of the illustrative embodiment shown in FIGS. 9i and 9j and described above.

As a result of the forgoing descriptions, the present disclosure provides various methods and systems that may be employed to test and evaluate the metallization layers of a BEOL metallization system and the pillar bumps formed thereabove.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
performing a lateral force test on a pillar bump formed above a metallization system of a semiconductor chip, said lateral force test comprising contacting a side of said pillar bump with a test probe while moving said test probe at a substantially constant speed that is less than approximately 1 µm/sec along a path that is oriented at a substantially non-zero angle relative to a plane of said metallization system, wherein said substantially non-zero angle is established so that said test probe is moving substantially away from said metallization system and so that a force imposed on said pillar bump by said test probe during said lateral force test comprises a component that is directed away from and induces a tensile load on said metallization system; and
determining a behavioral interaction between said pillar bump and said metallization system during said lateral force test.

2. The method of claim 1, further comprising orienting said plane of said metallization system at a substantially non-zero angle relative to a horizontal plane during said lateral force test.

3. The method of claim 1, further comprising moving said test probe at a substantially constant speed that is less than approximately 0.1 µm/sec.

4. The method of claim 1, wherein determining said behavioral interaction between said pillar bump and said metallization system comprises:
measuring a force imposed on said pillar bump by said test probe and a distance traveled by said test probe during a duration of said lateral force test; and
generating a force/distance response curve from said measured force and distance traveled.

5. The method of claim 1, further comprising generating a comparative behavioral interaction curve and comparing said behavioral interaction between said pillar bump and said metallization system to said comparative behavioral interaction curve.

6. The method of claim 5, wherein comparing said behavioral interaction between said pillar bump and said metallization system to said comparative behavioral interaction curve comprises determining a material strength of at least one material comprising said metallization system.

7. The method of claim 5, wherein generating said comparative behavioral interaction curve comprises:
performing a first lateral force test on each of a plurality of first pillar bumps formed above a first metallization system of a first semiconductor chip, wherein performing each of said first lateral force tests comprises contacting a side of each one of said plurality of first pillar bumps with a first test probe while moving said first test probe at a first substantially constant speed that is less than approximately 1 µm/sec;
measuring a force imposed on each one of said plurality of first pillar bumps by said first test probe and a distance traveled by said first test probe during a duration of each respective first lateral force test; and
generating said comparative behavioral interaction curve using said measured force and distance data from each of said first lateral force tests.

8. The method of claim 7, wherein moving said first test probe comprises moving said first test probe along a path that is substantially parallel to a plane of said first metallization system during each respective first lateral force test.

9. The method of claim 1, wherein said metallization system comprises a plurality of metallization layers, and wherein at least one of said metallization layers comprises one of a low-k dielectric material and an ultra-low-k dielectric material.

10. The method of claim 1, wherein performing said lateral force test comprises contacting a surface of said pillar bump with a test probe comprising a test probe tip that is adapted to grip said surface of said pillar bump during said lateral force test.

11. The method of claim 10, wherein performing said lateral force test comprises contacting said surface of said pillar bump with a test probe comprising a wedge shaped test probe tip.

12. The method of claim 10, wherein performing said lateral force test comprises contacting said surface of said pillar bump with a test probe comprising a serrated test probe tip.

13. The method of claim 1, further comprising forming an asymmetrically shaped notch in said pillar bump during said lateral force test.

14. A method, comprising:
performing a first lateral force test on a first pillar bump formed above a first metallization system of a first semiconductor chip, said first lateral force test comprising contacting said first pillar bump with a first test probe while moving said first test probe at a substantially constant speed that is less than approximately 0.1 µm/sec along a path that is oriented at a substantially non-zero angle relative to a plane of said metallization system, wherein said substantially non-zero angle is established so that said test probe is moving substantially away from said metallization system and so that a force imposed on said first pillar bump by said test probe during said first lateral force test comprises a component that is directed away from and induces a tensile load on said metallization system;

determining a first behavioral interaction between said first pillar bump and said first metallization system during said first lateral force test;

generating a comparative behavioral interaction curve representing a behavioral interaction between a second metallization system of a second semiconductor chip and a plurality of second pillar bumps formed thereabove; and comparing said first behavioral interaction to said comparative behavioral interaction curve.

15. The method of claim 14, wherein determining said first behavioral interaction between said first pillar bump and said first metallization system comprises measuring said force imposed on said first pillar bump by said first test probe and a distance traveled by said first test probe during a duration of said first lateral force test, and generating a first force/distance response curve from said measured force and distance traveled.

16. The method of claim 14, wherein said comparative behavioral interaction curve comprises a first curve portion that occurs immediately after a second test probe contacts one of said plurality of second pillar bumps and a second curve portion that occurs immediately following said first curve portion, said first curve portion illustrating a substantially non-linear force/distance relationship and said second curve portion illustrating a substantially linear force/distance relationship.

17. The method of claim 14, further comprising performing a second lateral force test on at least one additional pillar bump formed above said first metallization system, determining a second behavioral interaction between said at least one additional pillar bump and said first metallization system during a duration of said second lateral force test, and comparing said second behavioral interaction to said comparative behavioral interaction curve.

18. A method, comprising:
performing a first lateral force test on each of a plurality of first pillar bumps formed above a first metallization system of a first semiconductor chip, wherein performing each of said first lateral force tests comprises contacting a side of each one of said plurality of first pillar bumps with a first test probe while moving said first test probe at a first substantially constant speed that is less than approximately 1 µm/sec;

measuring a force imposed on each one of said plurality of first pillar bumps by said first test probe and a distance traveled by said first test probe during a duration of each respective first lateral force test;

generating a comparative behavioral interaction curve using said measured force and distance data from each of said first lateral force tests;

performing a second lateral force test on a second pillar bump formed above a second metallization system of a second semiconductor chip, said second lateral force test comprising contacting a side of said second pillar bump with a second test probe while moving said second test probe at a second substantially constant speed that is less than approximately 1 µm/sec along a path that is oriented at a substantially non-zero angle relative to a plane of said second metallization system;

measuring a force imposed on said second pillar bump by said second test probe and a distance traveled by said second test probe during a duration of said second lateral force test;

determining a behavioral interaction between said second pillar bump and said second metallization system during said second lateral force test using said measured force imposed on said second pillar bump and said distance traveled by said second test probe during said duration of said second lateral force test; and comparing said behavioral interaction between said second pillar bump and said second metallization system to said comparative behavioral interaction curve.

19. The method of claim 18, wherein said substantially non-zero angle of said path of said second test probe is established so that said second test probe is moving substantially away from said second metallization system and so that a force imposed on said second pillar bump by said second test probe during said second lateral force test comprises a component that is directed away from and induces a tensile load on said second metallization system.

20. The method of claim 19, wherein moving said first test probe comprises moving said first test probe along a path that is substantially parallel to a plane of said first metallization system during each respective first lateral force test.

* * * * *